(12) United States Patent
Huang et al.

(10) Patent No.: US 8,608,920 B2
(45) Date of Patent: Dec. 17, 2013

(54) ELECTROCHEMICAL BIOSENSOR STRIP AND METHOD FOR IDENTIFYING A CORRESPONDING BIOSENSING DEVICE BY SAID STRIP

(75) Inventors: Wen-Jung Huang, Luzhu Township, Taoyuan County (TW); Chia-Chi Wu, Kaohsiung (TW); Chia-Chin Yang, Luzhu Township, Taoyuan County (TW); Chao-Wang Chen, Taipei (TW)

(73) Assignee: Taidoc Technology Corporation, New Taipei (TW)

( * ) Notice: Subject to any disclaimer, the term of this patent is extended or adjusted under 35 U.S.C. 154(b) by 258 days.

(21) Appl. No.: 12/961,692

(22) Filed: Dec. 7, 2010

(65) Prior Publication Data
US 2011/0139635 A1 Jun. 16, 2011

(30) Foreign Application Priority Data

Dec. 14, 2009 (TW) ............................... 98142807 A
Feb. 11, 2010 (TW) ............................... 99104625 A

(51) Int. Cl.
*G01N 27/327* (2006.01)
(52) U.S. Cl.
USPC ...................... 204/403.02; 204/403.01; 435/4
(58) Field of Classification Search
USPC ............. 204/403.01–403.15; 205/777.5, 778, 205/792; 435/4–40.52; 422/68.1–98
See application file for complete search history.

(56) References Cited

U.S. PATENT DOCUMENTS

| | | | |
|---|---|---|---|
| 5,038,021 A * | 8/1991 | Uchigaki et al. | ............... 235/375 |
| 7,514,040 B2 | 4/2009 | Wu | |
| 2003/0204313 A1 | 10/2003 | Ou-Yang | |
| 2006/0144704 A1 * | 7/2006 | Ghesquiere et al. | ..... 204/403.01 |
| 2006/0182658 A1 * | 8/2006 | Wu et al. | ...................... 422/68.1 |
| 2008/0060196 A1 * | 3/2008 | Wang et al. | ..................... 29/854 |
| 2010/0170791 A1 * | 7/2010 | Lee | ........................ 204/403.01 |

* cited by examiner

*Primary Examiner* — Susan D Leong
(74) *Attorney, Agent, or Firm* — Chun-Ming Shih

(57) ABSTRACT

The present invention relates to an electrochemical biosensor strip comprising a base which has a front side and a back side, an electrode system on the front side of said base, a code-recognition element on one end of the back side of said base, a cover which is located on said electrode system, and a reaction area which is in touch with said electrode system for a reaction to take place. By forms of said code-recognition element provided in the present invention, a biosensing device will automatically choose a specific set of calibration code corresponding to a particular batch of the electrochemical biosensor strip while coupling to the strip. Hence, the present invention eliminates the calibration step carried out by users and simplifies the measuring procedure, avoiding the inaccurate results due to the omission or improper operation of the calibration step by users. The present invention further relates to a method for identifying a corresponding biosensing device by using a ratio of lengths of each length-changeable area of the strip.

29 Claims, 16 Drawing Sheets

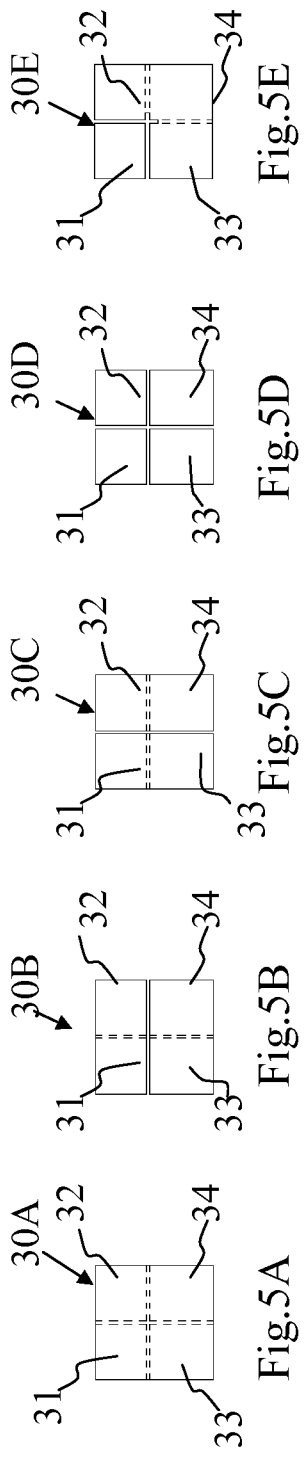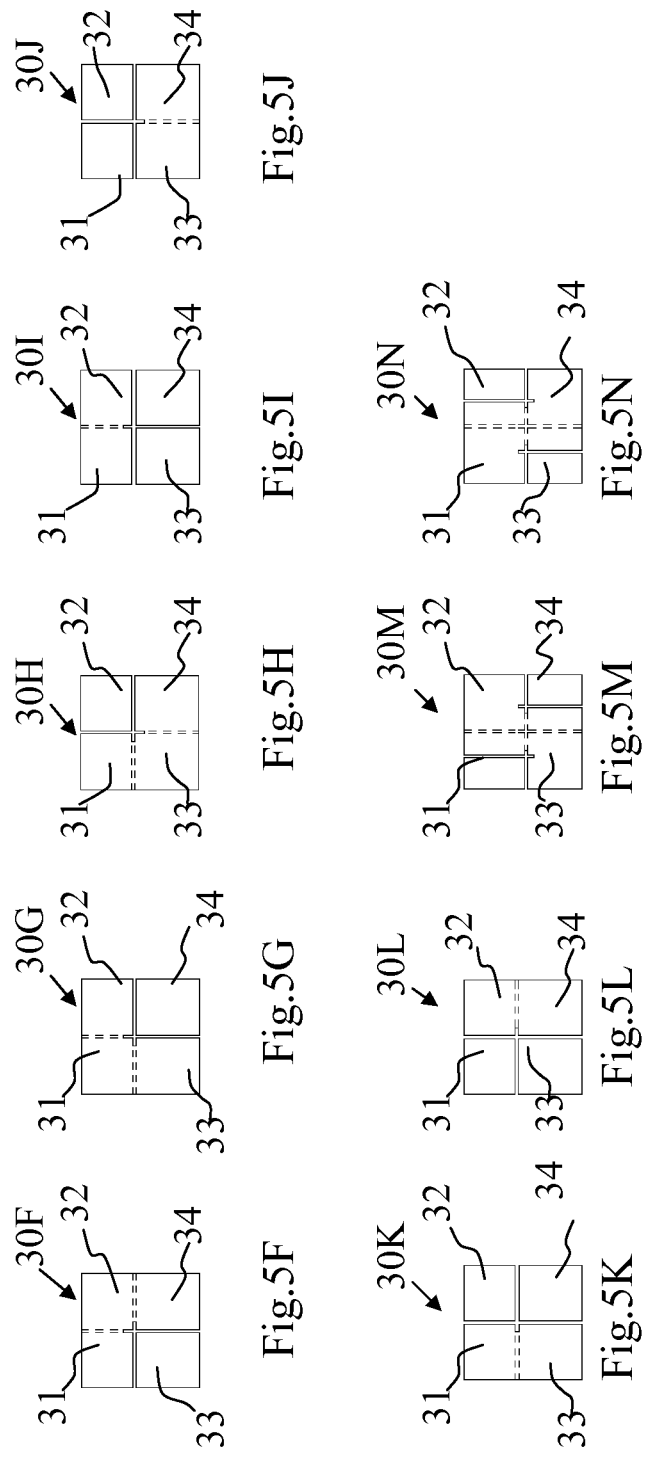

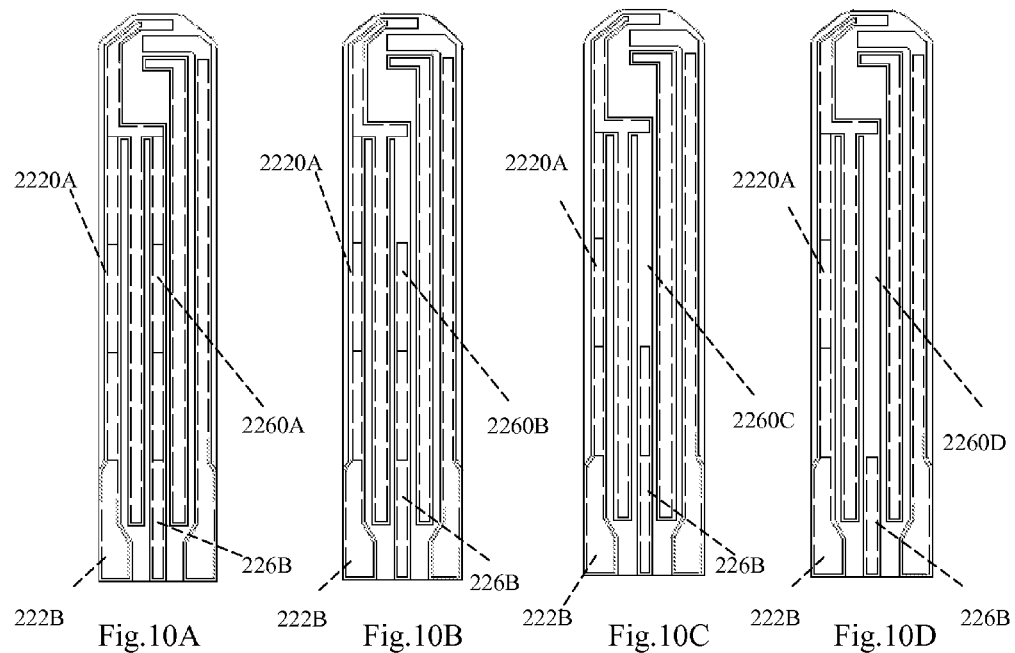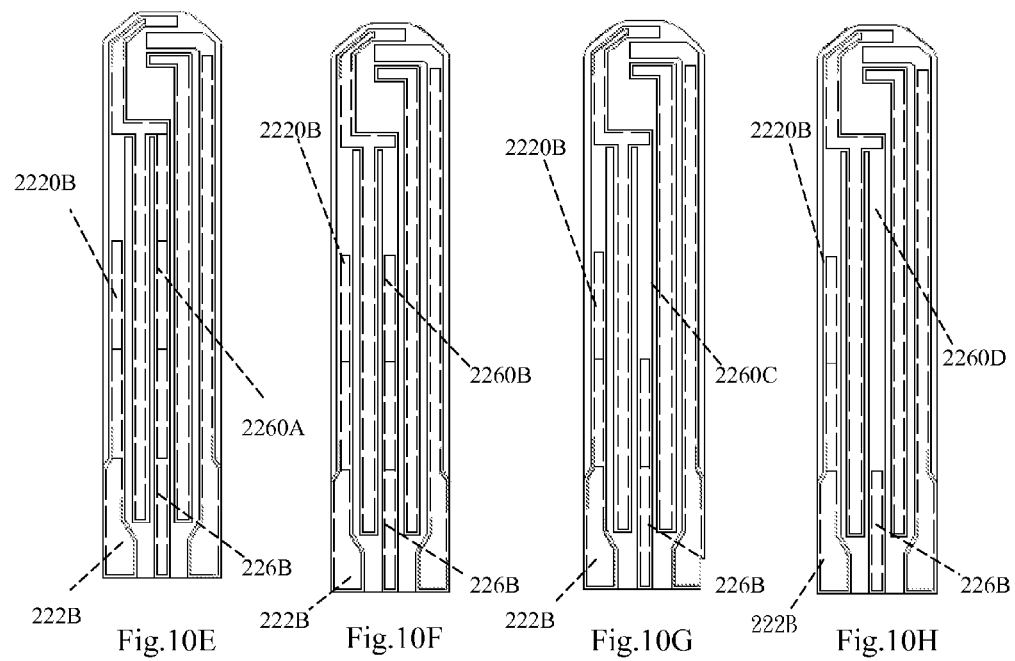

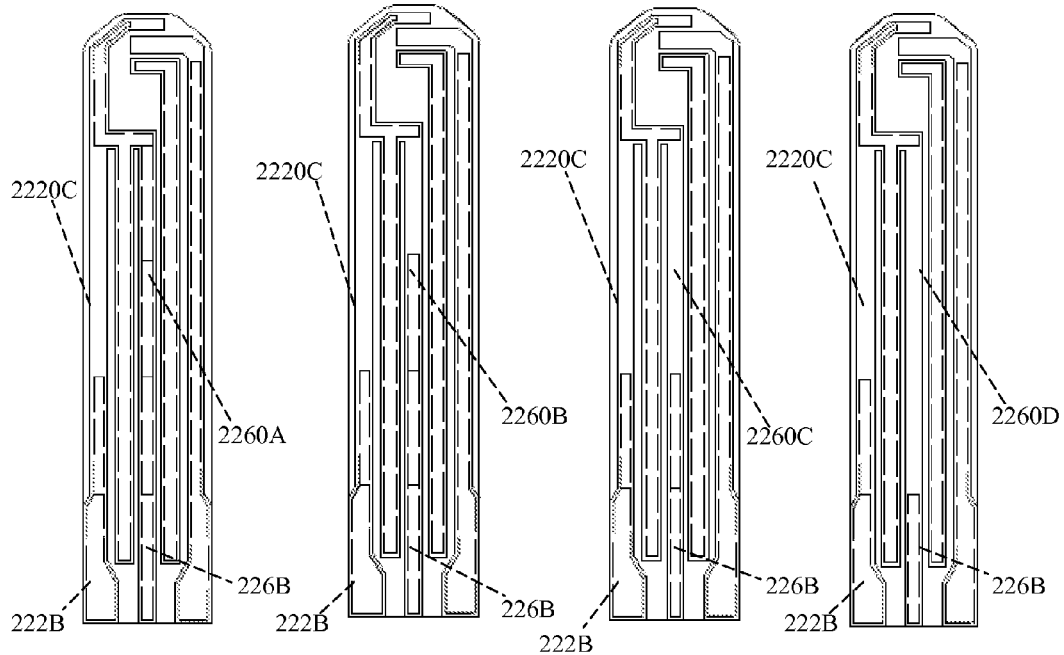
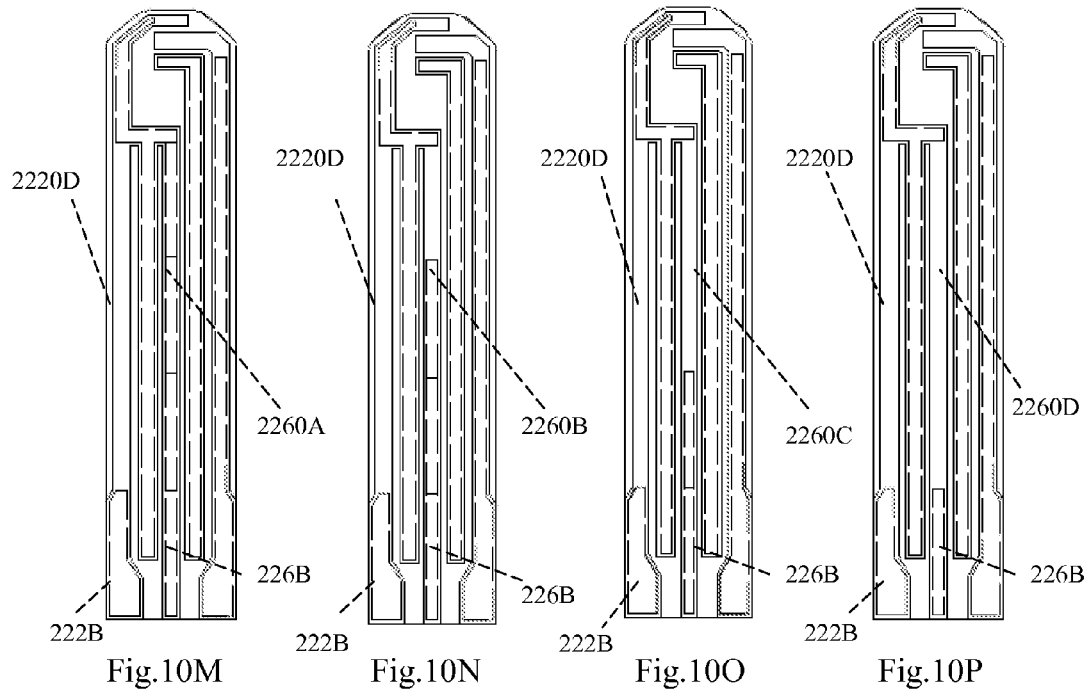

ELECTROCHEMICAL BIOSENSOR STRIP AND METHOD FOR IDENTIFYING A CORRESPONDING BIOSENSING DEVICE BY SAID STRIP

BACKGROUND OF THE INVENTION

1. Field of the Invention

In general, the present invention relates to an electrochemical biosensor strip, and in particular, to an electrochemical biosensor strip including a code-recognition element on one end of a back side of a base for avoiding calibration steps by users. The present invention further relates to a method for identifying a corresponding biosensing device, in particular to a method for identifying a corresponding biosensing device by using a ratio of lengths of each length-changeable area of the strip.

2. Description of the Related Art

Since the improvement of science and technology, many test processes operated in hospital in the past may now be operated at home. In market, many disposable biosensor strips are suitable for nonprofessionals to use and can be operated by users at home without pollution issue. The accurate data can be measured when the biosensor strip cooperated with an appropriate meter.

Taking blood glucose detecting technology as an example, the glucose meter becomes one of common POCT, point of care test, health-care devices in both home-care and hospital-care field.

Nowadays, most glucose meters on market are created based on the theory of Amperometric-electrochemistry. After blood glucose reacts with an enzyme at the electrochemical biosensor strip, electrons release during the forward reaction, and therefore the change of the current flow occurs. Then, by using the glucose meter, the change of the current flow is converted into a value of the blood glucose concentration.

Conventional electrochemical biosensor strip has a base, an electrode system, a reaction area and a cover. The electrode system is laid on the base and comprises an anode electrode and a cathode electrode independently and separately electrically disconnecting with each other. An insulating layer is laid down onto one portion of the electrode system, and therefore one portion of the electrode system is exposed. One end of the exposed portion of the anode and cathode electrode respectively forms a working electrode and a reference electrode, while the other end of the exposed portion of the anode and cathode electrode electrically connect with a meter. The reaction area, which is made depending on different design, is laid onto the working electrode and the reference electrode, and the cover is laid onto the reaction area.

After a sample received into the strip, the sample reacts with a material of the reaction area to produce an electrical signal which is then transferred from the working electrode and the reference electrode to the anode electrode and the cathode electrode of the other end. The coupled meter receives the electrical signal and calculates the signal to convert into an analyte concentration and shows on a display.

However, due to conventional electrochemical biosensor strips have been made by batch production, the variables during batch production will cause the variety of the strips from batch to batch, such as the volume of the working electrodes and the reference electrodes, the quantity of the enzyme and so on. All of above reasons will cause inaccurate results. To avoid this problem, producers set a specific set of calibration code corresponding to the strips per batch to confirm the consistency of the analyzing value before they sell the meters and the strips. The function of calibration in glucose meters is to confirm that the result will not be affected due to different batch of strips.

Main code-calibration methods have been used on market, such as chip-setting method, strip-number comparing method and so on. Take chip-setting method for example. A provided chip must be used to calibrate the code in the glucose meter before the strip inserting to. However, patients often forget to use the chip to calibrate the code, and then cause an inaccurate result. Such method is similar to the disclosure in U.S. application No. 2003204313. The strip-number comparing method described in U.S. Pat. No. 7,514,040 discloses a biosensing meter which not only stores sets of calibration code therein but also receives a code card to store new parameter or downloads new parameter from an internet. One set of the calibration code matched to the batch of the strips must be selected out before users doing the measuring process.

As described above, no matter what kind of code-calibration methods used in glucose meter, all of above must be needed extra calibration steps carried out by users. These cause the complexity during the measuring procedure. Once users do not do the calibration steps correctly, they won't get the accurate results.

Therefore, how to simplify code-calibration steps before measurement and still maintain the accurate results becomes an issue to the producers.

Besides, to ensure that users can use the electrochemical biosensor strips correctly, different strips are usually specific to their own corresponding biosensing device respectively. In other word, biosensing device can carry out the measuring process only when the specific strip insert into the corresponding biosensing device.

Producers in designing electrochemical biosensor strips need to produce varieties of electrochemical biosensor strips due to different purposes, analytes, costumers, or users to meet the market's need, and therefore, kinds of strips and biosensing devices are produced on market. The variety and the complexity of strips and devices are increasing. Hence, how to identify a biosensing device corresponding to a specific electrochemical biosensor strip effectively and simply also becomes an issue for producers and users.

SUMMARY OF THE INVENTION

The specification and practices of the present invention disclosed as following. It is intended that the specification and embodiments to be considered as exemplary only.

As used herein, the phrase "Biosensing device" means a device couples to an electrochemical biosensor strip of the present invention for measuring a specific material concentration in a sample, such as meters for measuring the concentration of blood glucose, cholesterol or uric acid and so on.

As used herein, the phrase "Sensor end" means one end of the electrochemical biosensor strip of the present invention that can be in touch with a biosensing device.

As used herein, the phrase "Reaction end" means one end of the electrochemical biosensor strip of the present invention opposite to the sensor end, which reacts with a sample or where a reaction area is located.

As described in the prior art, in order to simplify the calibration steps and still maintain the accuracy of results, an aspect of the present invention is provided an electrochemical biosensor strips.

The electrochemical biosensor strip in accordance with the present invention comprises a code-recognition element on one end of a back side of a base. The code-recognition element is used to make the biosensing device automatically choose a specific set of calibration code corresponding to a particular batch of the electrochemical biosensor strip while coupling to the strip. Hence, one aspect of the present invention is to eliminate the calibration step carried out by users and simplify the measuring procedure, and avoid the inaccurate results due to the omission or improper operation of the calibration steps by users.

An electrochemical biosensor strip in accordance with the present invention comprises a base having a front side and a back side, an electrode system on the front side of the base, a code-recognition element on one end of the back side of the base for corresponding to a specific set of calibration code, a cover located on the electrode system, and a reaction area in touch with the electrode system for a reaction to take place.

In a preferred embodiment of the present invention, the code-recognition element of the electrochemical biosensor strip includes at least four blocks. Hence, the code-recognition elements have different forms which can be formed depending on the connection or disconnection among blocks. Each form of the code-recognition element corresponds to one specific set of calibration code respectively. Therefore, a biosensing device coupling to the strip will automatically choose a specific set of calibration code corresponding to the particular batch of the electrochemical biosensor strip that have the particular code-recognition element.

In a more preferred embodiment of the present invention, the code-recognition element of the electrochemical biosensor strip includes a first block, a second block, a third block and a fourth block. Depending on the disconnection or connection among the first block, the second block, the third block and the fourth block, there are fourteen forms of code-recognition elements formed. Each form of the code-recognition elements corresponds to a specific set of calibration code respectively.

The code-recognition element of the electrochemical biosensor strip in accordance with the present invention may be composed of conducting materials. In a preferred embodiment of the present invention, the code-recognition element is composed of carbon, and each block is defined by laser etching or by knife etching. In a preferred embodiment of the present invention, the code-recognition element is disposed on the back side of the base at the sensor end.

Another aspect of the present invention is to identify a biosensing device corresponding to a specific electrochemical biosensor strip effectively and simply, and therefore, the electrode system of the electrochemical biosensor strip in accordance with the present invention comprises at least three electrodes, and at least one of them has a length-changeable area.

The length-changeable area is used for identifying a particular biosensing device corresponding to the strip. Due to the length-changeable area of the electrodes can be adjusted to different lengths; the resistance value of the electrodes can be adjusted. By measuring the resistance value while the biosensor strip couples into a biosensing device, the particular biosensing device corresponding to the particular strip can be identified. Preferably, four forms of electrodes can be formed depending on four different lengths of the length-changeable areas, and therefore, four biosensing devices can be identified. In a more preferred embodiment of the present invention, the electrode having the length-changeable area can be regarded as a reference electrode.

In another preferred embodiment of the present invention, the electrode system comprises at least three electrodes and at least two of the electrodes have a length-changeable area respectively. By using a ratio of the lengths of each length-changeable area of the two electrodes, the particular biosensing device corresponding to the particular strips can be identified.

Preferably, the ratio of the lengths of each length-changeable area is used for identifying the biosensing device corresponding to the strip, and the ratio is one of the ratios in a range of 1:10 to 10:1.

In another more preferred embodiment of the present invention, four forms of the lengths of each length-changeable area of the two electrodes can be formed respectively, and the ratio of the lengths of each length-changeable area is one of the ratios in a range of 1:4 to 4:1.

According to the resistance formula as following:
$R = \rho(L/A)$, where $\rho$ is resistivity of a conductor, L is the length of the conductor and A is the cross-sectional area of the conductor.

Hence, when the resistivity and the cross-sectional area of the conductor are constant, the resistance value of the conductor and the length of the conductor (L) are in direct proportion.

Besides, the resistivity of the conductor has no relation to the cross-sectional area or the length of the conductor; it depends on what conducting materials the conductor is.

In a preferred embodiment of the present invention, the materials of each electrode of the electrode system are uniform, and therefore, the resistivity of each electrode is considered the same. Each electrode of the electrode system is disposed on the base by screen-printing, and therefore, the cross-sectional area of each electrode of the electrode system of the strip is considered the same. Hence, the resistance value of each electrode of the electrochemical biosensor strip is directly proportional to the length of the electrode of the electrochemical biosensor strip according to the formula describe above.

The electrode system of the electrochemical biosensor strip in accordance with the present invention comprises a silver layer and a carbon layer. The carbon layer is stacked onto the silver layer, and each electrode of the electrode system comprises a correlated electrode of the carbon layer and a correlated electrode of the silver layer. For example, a first electrode of the electrode system is composed of a first electrode of the silver layer and a first electrode of the carbon layer.

In a preferred embodiment of the present invention, the electrode system includes five electrodes, wherein two of them have a length-changeable area respectively, and the length-changeable area is part of the electrode of the silver layer, therefore, there is a ratio of the lengths of each length-changeable area of the two electrodes. The ratio is used for identifying a particular biosensing device corresponding to the strip and is one of the ratios in a range of 1:10 to 10:1.

In another more preferred embodiment of the present invention, four forms of the lengths of each length-changeable area can be formed. And the ratio of the lengths of each length-changeable area of the two electrodes is one of the ratios in a range of 1:4 to 4:1.

Due to each electrode of the silver layer and each electrode of the carbon layer are disposed in parallel connection to form each electrode of the electrode system, and according to the resistance formula in parallel circuit as following:

$$R = (R1 \times R2)/(R1+R2).$$

When R1 is far less than R2, the resistance value (R) of the parallel circuit tends near R1.

In the present invention, because of the resistivity of silver, which is about $1.6 \times 10-8 \, \rho/\Omega m$, is extremely small, the resistance value of the electrode of the silver layer is far less than the resistance value of the electrode of the carbon layer. Hence, the total resistance value of the electrode of the electrode system tends near the resistance value of the electrode of the silver layer according to the resistance formula in parallel circuit described above.

The length-changeable area in accordance with the present invention is part of the silver layer.

By emptying out a particular length of the length-changeable area of the electrode of the silver layer, such as empty out one-forth, half or three-forth of full length of the length-changeable area, only the carbon layer will be left behind. Hence, the resistance value of the electrode of the silver layer can be changed due to different emptied-lengths of length-changeable area of the electrode of the silver layer.

Accordingly, the resistance value in the parallel circuit of the electrodes of the carbon and silver layer tends near the resistance value of the electrode of the silver layer, and therefore, at the circumstances that portion of the length-changeable area of the electrode of the silver layer is being emptied out, the total resistance value of the electrode of the electrode system is near directly proportional to the length of the electrode of the carbon layer left behind, or the emptied-length of the length-changeable area of the electrode of the silver layer. For example, if the emptied-length of the first electrode of the silver layer is twice longer than the emptied-length of the second electrode of the silver layer, then the resistance value of the first electrode of the silver layer is closely twice larger than that of the second electrode of the silver layer.

Accordingly, kinds of electrodes with different lengths of length-changeable area can be designed for controlling the resistance value of each electrode, and by calculating the ratio of the resistance value of the two electrodes on the same strip for excluding the effect of resistivity and cross-sectional area of the electrodes. Further, simplify the ratio of the resistance value as the ratio of the lengths of each length-changeable area of the two electrodes for identifying a particular biosensing device corresponding to the strip will prevent from the error caused by manufacture differences between each batch strips, such as width, depth or uniformity of the carbon layer.

The five electrode of the electrode system of the electrochemical biosensor strip in accordance with the present invention from one side to another side in a order are a first electrode, a second electrode, a third electrode, a fourth electrode and a fifth electrode.

In a preferred embodiment of the present invention, the first electrode and the third electrode of the silver layer have a length-changeable area respectively, and there is a ratio of the length of the length-changeable area of the first electrode of the silver layer to that of the third electrode of the silver layer. The above mentioned ratio is used for identifying a biosensing device corresponding to the strip, which can be one of the ratios in a range of 1:10 to 10:1.

In another more preferred embodiment of the present invention, four forms of lengths of each length-changeable area of the first electrode and the third electrode of the silver layer can be formed respectively. The ratio of the lengths of the two length-changeable areas is one of the ratios in a range of 1:4 to 4:1. Furthermore, the first electrode, the second electrode and the third electrode of the electrode system are formed in a short-circuit structure.

By adjusting the ratio of the lengths of each length-changeable area of the strip, kinds of strips can be formed and therefore can be used to correspond to particular biosensing devices. For instance, an "A" biosensing device is set to correspond to the strip with a ratio of lengths of the length-changeable areas which is 1:1, and a "B" biosensing device is set to correspond to the strip with a ratio of lengths of the length-changeable areas which is 1:2, and so on. Besides, the length-changeable area can also be disposed in other electrodes of the silver layer if it is needed.

For instance, the first electrode and the second electrode of the silver layer have a length-changeable area respectively, or the second electrode and the third of the silver layer have a length-changeable area respectively, which can correspond to a particular biosensing device respectively.

The methods described above can also be combined, and therefore, kinds of electrodes of the strips of the present invention can be provided for corresponding to varieties of biosensing devices.

In the electrochemical biosensor strip in accordance with the present invention, the electrodes of the electrode system are disposed at more inner position to save a distance between an end of the electrode system and the base at the sensor end for preventing from turning on the biosensing device before the strip insert into the device appropriately, and the distance is about 0.1 to 1 millimeter.

The electrode system of the electrochemical biosensor strip in accordance with the present invention includes at least three electrodes, and at least one of them is regarded as a reference electrode and at least another one of them is regarded as a working electrode.

In a preferred embodiment, the electrode system includes five electrodes, and two of them connect with each other to form a short circuit and are regarded as one reference electrode and another two of them are regarded as a working electrode respectively for measuring the concentration of blood glucose and blood hematocrit in a sample. The last one of the electrodes is regarded as a detecting electrode for detecting whether the sample enters into the reaction area completely or not.

In a more preferred embodiment, the electrode system includes five electrodes, wherein the second electrode of the electrode system and the third electrode of the electrode system connect with each other to form a short circuit and regarded as one reference electrode, the fourth electrode of the electrode system is regarded as a detecting electrode, and the first electrode and the fifth electrode of the electrode system are regarded as a working electrode respectively.

In yet another more preferred embodiment, the electrode system includes five electrodes, and the first electrode and the second electrode connect with each other to form a short circuit and regarded as one reference electrode, the third electrode is a detecting electrode, and the fourth electrode and the fifth electrode are a working electrode respectively.

The electrochemical biosensor strip in accordance with the present invention further comprises an isolation layer laid onto the electrode system and part of the base. The isolation layer at the reaction end has a first recess opening toward the reaction end in a longitudinal direction. The isolation layer further has an opening next to the first recess. The opening corresponds to the reaction area and disconnects with the first recess.

The cover of the electrochemical biosensor strip in accordance with the present invention has a hole and a gap. The hole corresponds to the opening at the isolation layer for air flowing. The gap is disposed at the reaction end. In a preferred embodiment, the shape of the gap is semicircular or semi-elliptical.

Furthermore, the electrochemical biosensor strip in accordance with the present invention has a rough unit disposed at an outer side of the carbon layer at the reaction end. The rough unit is a multiple-straight-line unit to increase the roughness of the base, prevent the material at the reaction area from separating apart and to increase the accuracy of measurement.

The electrochemical biosensor strip in accordance with the present invention further comprises a glue layer between the isolation layer and the cover for joining the isolation layer and the cover together. The glue layer has a second recess corresponding to the first recess and the opening of the isolation layer.

The electrochemical biosensor strip in accordance with the present invention further comprises an insulating layer between the electrode system and the isolation layer. The insulating layer has a third recess corresponding to the first recess and the opening of the isolation layer.

In another aspect of the present invention is provided a method for identifying a corresponding biosensing device by using the strip with at least two electrodes respectively having a length-changeable area described above. The method comprises contacting the electrode system with a biosensing device, detecting resistance values of the electrodes having a length-changeable area respectively and obtained the resistance values, calculating the resistance values according to a formula and obtained a final value, and confirming whether the final value is match to a predetermined value of the biosensing device or not. The final value therein is used for identifying a biosensing device corresponding to the electrochemical biosensor strip.

The method for indentifying a biosensing device of the present invention further comprises steps which are turning on the biosensing device if the final value is match to the predetermined value, and do not turn on the biosensing device if the final value is not match to the predetermined value. Herein, the term "match" means that the final value equals to the predetermined value or higher, or less than the predetermined value but in an accepted error range. And the term "not match" means that the final value is higher or less than the predetermined value and out of the accepted error range.

In yet another aspect of the present invention is provided a method for identifying a biosensing device by using the strip with at least two electrodes respectively having a length-changeable area as described above. The method comprises contacting the electrode system with a biosensing device, detecting the resistance values of the two electrodes having a length-changeable area respectively and obtained a first resistance value and a second resistance value, calculating a ratio of the first resistance value and the second resistance value, and confirming whether the ratio is match to a predetermined value of the biosensing device or not.

According to the above description about the length-changeable area of the electrode system, the first resistance value and the second resistance value are respectively in direct proportional to the emptied-lengths of the length-changeable areas of the two electrodes of the silver layer. Hence, the ratio of the two resistance values is almost equal to the ratio of the emptied-lengths of the length-changeable areas of the two electrodes of the silver layer. Preferably, the ratio is one of the ratios in a range of 0.1 to 10, and the ratio is used for identifying a biosensing device corresponding to the strip.

The method described above further comprises steps which are turning on the biosensing device if the ratio is match to the predetermined value, and do not turn on the biosensing device if the ratio is not match to the predetermined value. Herein, the terms "match" means that the ratio equals to the predetermined value or higher, or less than the predetermined value but in an accepted error range. And the terms "not match" means that the ratio is higher, or less than the predetermined value and out of the accepted error range.

According to the above descriptions, some advantages of the electrochemical biosensor strip in accordance with the present invention comparing to the prior art are listed below:

Firstly, the biosensing device will automatically choose the specific set of calibration code corresponding to the particular batch of the electrochemical biosensor strip when the electrochemical biosensor strip in accordance with the present invention couples to the particular biosensing device. Hence, the present invention eliminates the calibration step carried out by users and simplifies the measurement procedure, and avoids the inaccurate results due to the omission or improper operation of the calibration step by users.

Secondly, the cost for producing chips for calibration decreased.

Thirdly, the code-recognition element is disposed on the back side of the base for avoiding being disposed on the front side of the base as the electrode system disposed and this can decrease the complexity of device design and the cost of manufacture.

Fourthly, the convenience of use is increased by using the electrodes that can change the length or a ratio of the length of each length-changeable area for identifying a particular biosensing device corresponding to the strip.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will be further described, by way of example only, with reference to the accompanying drawings, in which:

FIGS. 5A to 5N are exploded views of forms of a code-recognition element of an electrochemical biosensor strip in accordance with the present invention.

FIGS. 10A to 10P are some forms of the electrodes of the third form of the electrode system referring to FIG. 8, and the length-changeable area is disposed at the first electrode and the third electrode of the electrode system.

DESCRIPTION OF THE PREFERRED EMBODIMENTS

Figure 1:
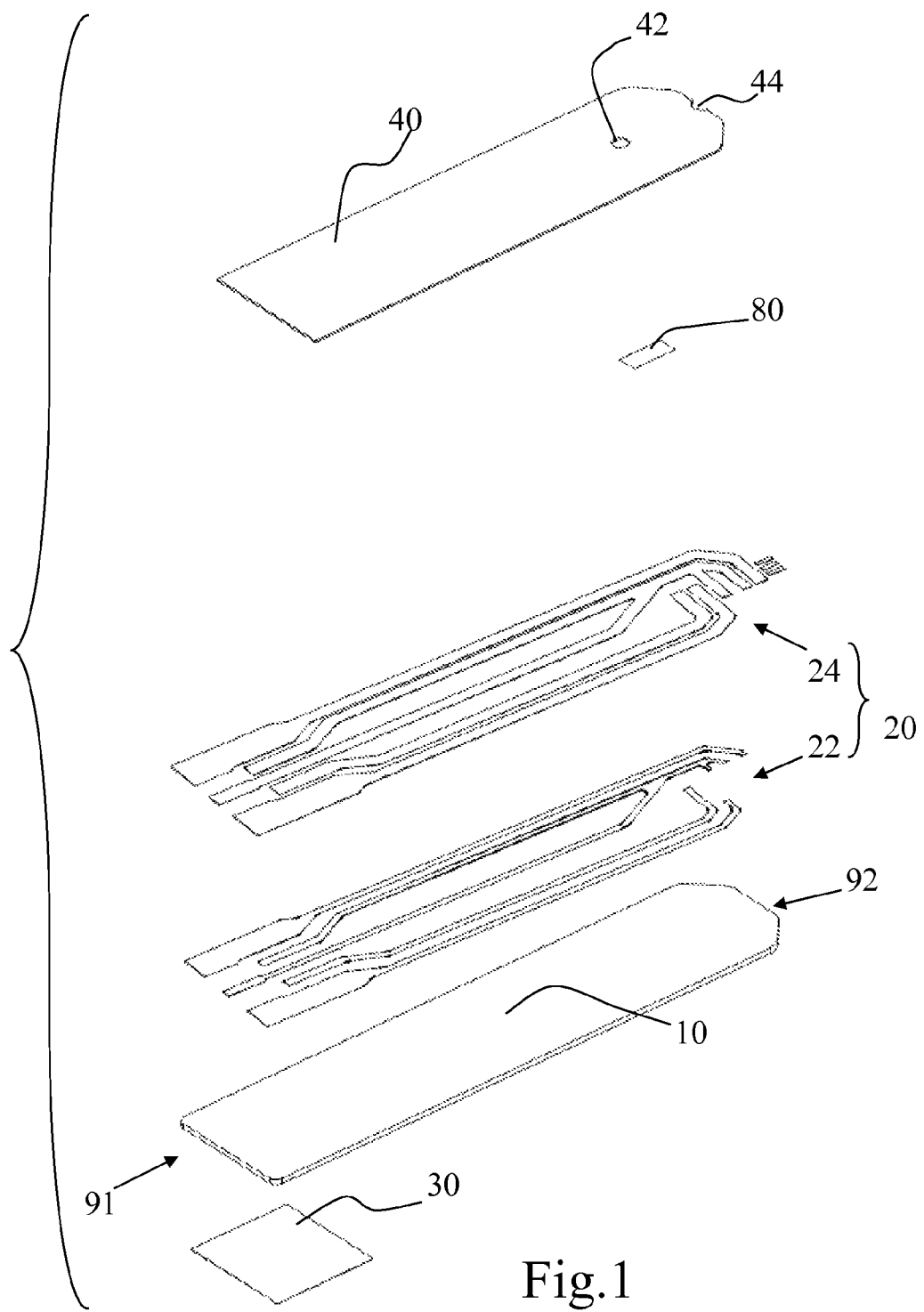
FIG. 1 is an exploded perspective view of an embodiment of an electrochemical biosensor strip in accordance with the present invention.

For the purposes of promoting an understanding of the principles of the invention, reference will now be made to the embodiment illustrated in the drawings, and specific language will be used to describe that embodiment. It will nevertheless be understood that no limitation of the scope of the invention is intended. Alterations and modifications in the illustrated device, and further applications of the principles of the invention as illustrated therein, as would normally occur to one skilled in the art to which the invention relates are contemplated, are desired to be protected. In particular, although the invention is discussed in terms of a blood glucose meter, it is contemplated that the invention can be used with devices for measuring other analytes and other sample types. Such alternative embodiments require certain adaptations to the embodiments discussed herein that would be obvious to those skilled in the art.

Figure 2:
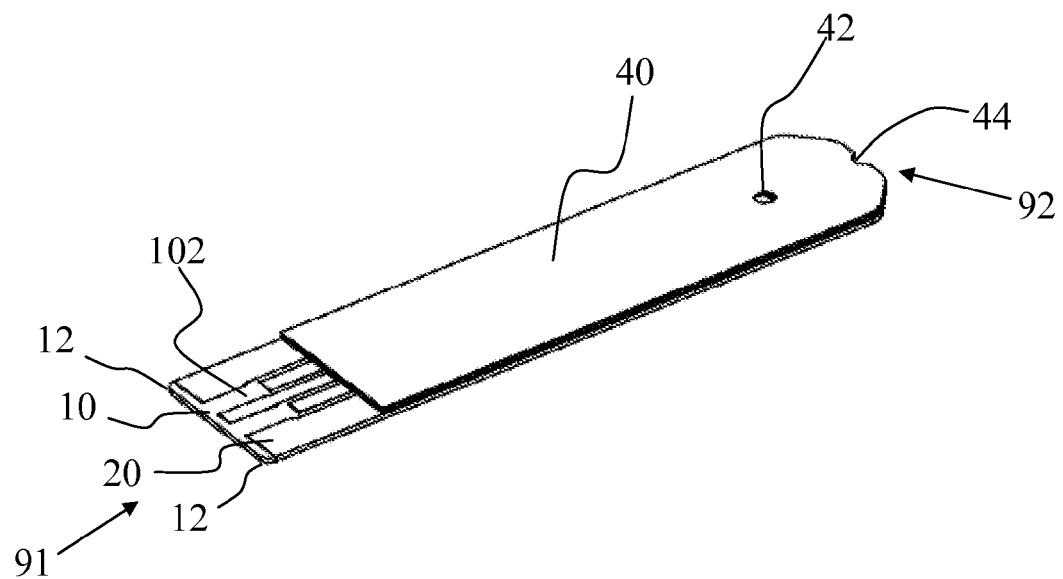
FIG. 2 is a perspective top view of the embodiment of the electrochemical biosensor strip in accordance with the present invention.
Figure 3:
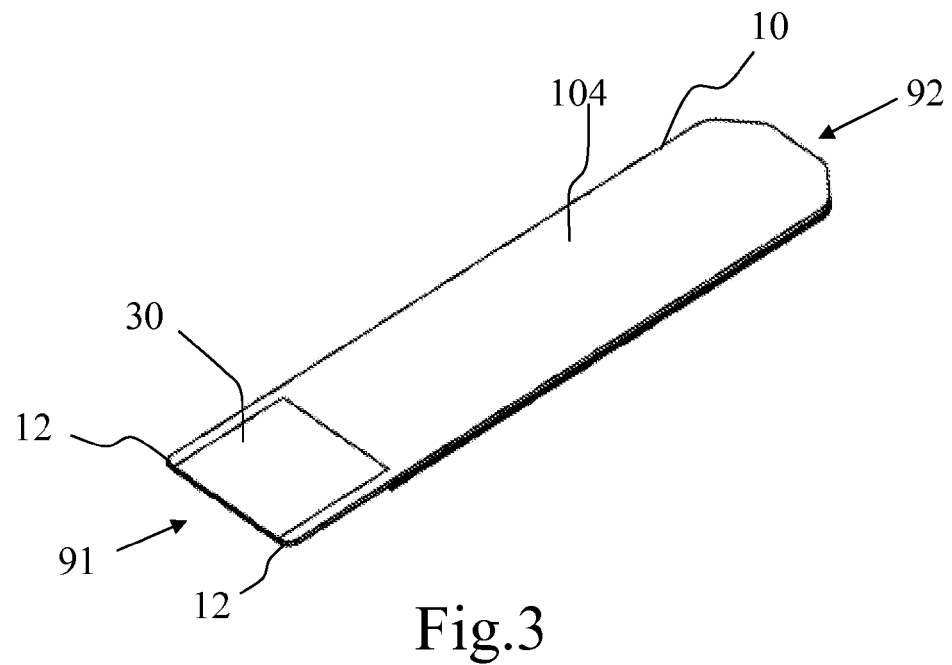
FIG. 3 is a perspective bottom view of the embodiment of the electrochemical biosensor strip in accordance with the present invention.

With reference to FIGS. 1, 2 and 3, the first embodiment of an electrochemical biosensor strip in accordance with the present invention includes a base (10) having a front side (102) and a back side (104), an electrode system (20) on the front side (102) of the base (10), a code-recognition element (30) on one end of the back side (104) of the base (10) for corresponding to a specific set of calibration code, a cover (40) located on the electrode system (20), and a reaction area (80) in touch with the electrode system (20) for processing a reaction. Besides, the electrochemical biosensor strip in accordance with the present invention may further comprises a sensor end (91) and a reaction end (92).

Accordingly, the base (10) may be shaped as a rectangle-shaped plate and preferably is electrically insulated. In a preferred embodiment of the present invention, four angles of the base (10) are blunt angles (12) for avoiding users from injury while operation. The electrode system (20) is covered over the front side (102) of the base (10) and the electrode system (20) includes a silver layer (22) and a carbon layer (24). The carbon layer (24) is laid onto the silver layer (22). The electrode system (20) includes at least three electrodes, and at least one of them is a working electrode and another one of them is a reference electrode. In a preferred embodiment, the electrode system (20) at the sensor end (91) are arranged in a longitudinal direction of the base (10) and parallel to each other for being in touch with the biosensing device to detect the variation of an electrochemical reaction.

In a preferred embodiment, the electrodes of the electrode system (20) are disposed at more inner position to save a distance between an end of the electrode system (20) and the base (10) at the sensor end (91) for preventing from turning on the biosensing device before the strip inserts into the device appropriately, and the distance is about 0.1 to 1 millimeter. More preferably, the distance is about 0.3 to 0.8 millimeter. The most preferably, the distance is about 0.5 to 0.6 millimeter.

With reference to FIG. 1, the cover (40) is laid onto the electrode system (20). The cover (40) has a hole (42) for gas flowing and a gap (44) at the sensor end (92). Preferably, the shape of the gap (44) is semicircular or semi-elliptical. By the design of the gap, the sample-entering surface area of the reaction area (80) increase, and therefore the sample may enter into the reaction area (80) not only from the lateral side of the strip in parallel direction but also from the top of the strip in other directions. And hence not only the use convenience but the sample-entering speed are increased. Therefore, the accuracy of test results can be increased.

The reaction area (80) of the electrochemical biosensor strip in accordance with the present invention is laid onto the base (10) and part of the electrode system (20), and which contains biologically active substance (such as enzyme), enzyme cofactors, stabilizer (such as polymer), and buffer and so on for reacting with the sample.

Figure 4B:
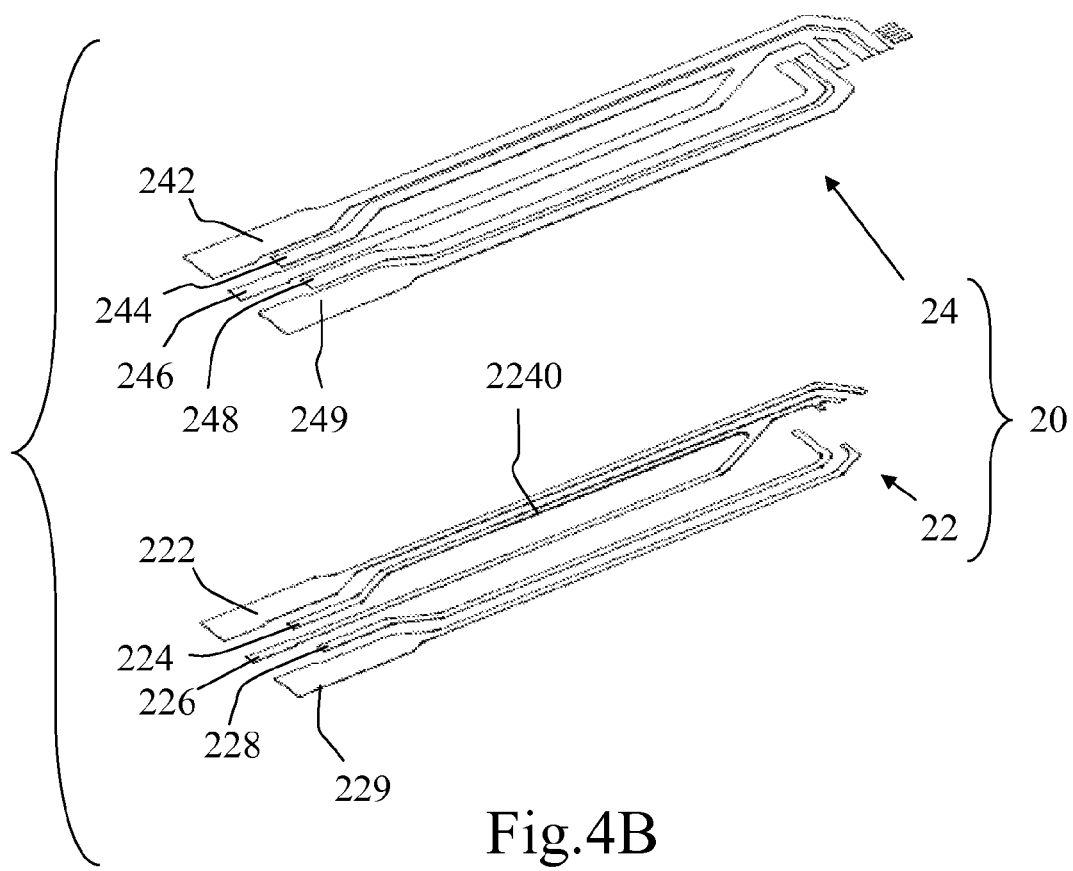
FIGS. 4A and 4B are exploded views of electrodes of a preferred embodiment of an electrochemical biosensor strip in accordance with the present invention.
Figure 4A:
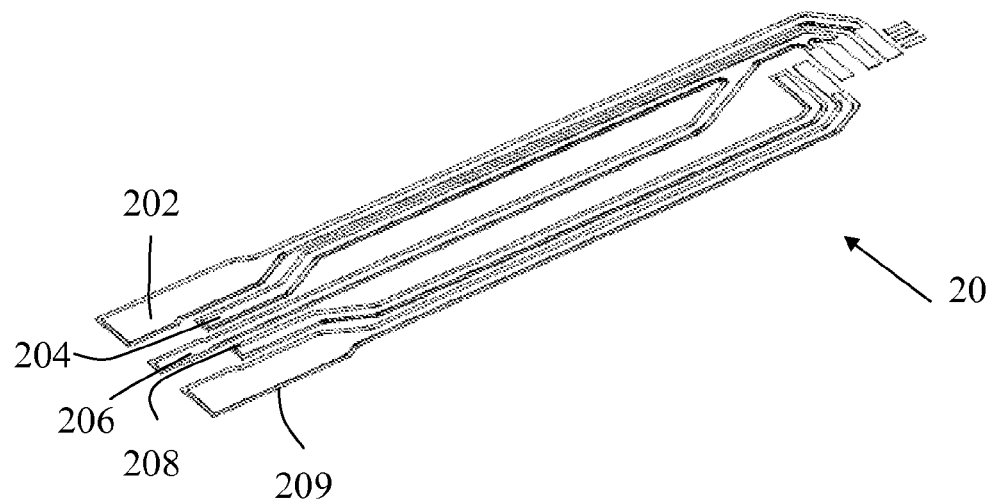

With reference to FIG. 4A, the electrode system (20) of the electrochemical biosensor strip in a preferred embodiment comprises five electrodes respectively named first electrode of the electrode system (202), second electrode of the electrode system (204), third electrode of the electrode system (206), fourth electrode of the electrode system (208) and fifth electrode of the electrode system (209). With reference to FIG. 4B, each electrode of the electrode system (20) is composed of a correlated electrode of the carbon layer (24) and a correlated electrode of the silver layer (22). The five electrodes of the carbon layer respectively named first electrode of the carbon layer (242), second electrode of the carbon layer (244), third electrode of the carbon layer (246), fourth electrode of the carbon layer (248) and fifth electrode of the carbon layer (249). The five electrodes of the silver layer respectively named first electrode of the silver layer (222), second electrode of the silver layer (224), third electrode of the silver layer (226), fourth electrode of the silver layer (228) and fifth electrode of the silver layer (229). One end of each of the five electrodes of the electrode system are all arranged in a longitudinal direction and parallel to each other, and the second electrode of the silver layer (224) has a length-changeable area (2240) therein.

Preferably, two of the five electrodes of the electrode system (20) connect with each other to form a short circuit. Referring to FIG. 4, in a more preferred embodiment, the second electrode of the electrode system (204) and the third electrode of the electrode system (206) connects with each other to form a short circuit and regarded as a reference electrode.

In a preferred embodiment, one of the five electrodes of the electrode system (20) is regarded as a detecting electrode for detecting whether a sample enters into the reaction area (80) perfectly or not. Referring to FIG. 4, in a more preferred embodiment, the fourth electrode of the electrode system (208) is regarded as a detecting electrode for detecting whether a sample enters into the reaction area (80) perfectly or not.

In a preferred embodiment, one of the five electrodes of the electrode system (20) is regarded as a working electrode for measuring blood glucose concentration in a sample. More preferably, the fifth electrode of the electrode system (209) is the working electrode for measuring the concentration of the blood glucose in a sample.

In a preferred embodiment, one of the five electrodes of the electrode system (20) is regarded as a working electrode for measuring the blood hematocrit in a sample. More preferably, the first electrode of the electrode system (202) is the working electrode for measuring the blood hematocrit in a sample.

The code-recognition element (30) of the electrochemical biosensor strip of the present invention is disposed on one end of the back side (104) of the base (10). Referring to FIGS. 1 and 3, in a preferred embodiment, the code-recognition element (30) is disposed on the back side (104) of the base (10) at the sensor end (91) and opposites to the electrode system (20) which is disposed at the front side (102) of the base (10) and is used for being in touch with a biosensing device for processing a code-recognition process.

Referring to FIGS. 5A to 5N, forms of the code-recognition elements (30) of the electrochemical biosensor strips of the present invention are provided. The code-recognition element (30) includes at least four blocks. In a preferred embodiment, the code-recognition element (30) includes four blocks respectively named first block (31), second block (32), third block and fourth block (34). Depending on the disconnection or connection among these blocks, there are fourteen forms of code-recognition elements (30) can formed. Each form of the code-recognition elements (30) corresponds to a specific set of calibration code. The disconnection or connection among blocks is defined by laser etching or knife etching. The double-dotted line as FIGS. 5A to 5N showed represents the connection among blocks and the double-solid line here represents the disconnection among blocks.

FIG. 5A shows a form of code-recognition element (30A) corresponding to a first set of calibration code, and the first block (31), second block (32), third block (33) and fourth block (34) of the code-recognition element (30A) connect with each other.

FIG. 5B and FIG. 5C show that two of the four blocks of the code-recognition element (30) connect with each other and the other two connect with each other but the two connected blocks disconnected with the other two connected blocks.

FIG. 5B shows a form of code-recognition element (30B) corresponding to a second set of calibration code, and the first block (31) and the second block (32) of the code-recognition element (30B) connect with each other. The third block (33) and the fourth block (34) of the code-recognition element (30B) connect with each other. Further, the first and second connected blocks (31, 32) disconnected with the third and fourth connected blocks (33, 34).

FIG. 5C shows a form of code-recognition element (30C) corresponding to a third set of calibration code, and the first block (31) and the third block (33) of the code-recognition element (30C) connect with each other. The second block (32) and the fourth block (34) of the code-recognition element (30C) connect with each other. Further, the first and third connected blocks (31, 33) disconnected with the second and fourth connected blocks (32, 34).

FIG. 5D shows a form of code-recognition element (30D) corresponding to a fourth set of calibration code, and the first block (31), the second block (32), the third block (33) and the fourth block (34) of the code-recognition element (30D) separately and independently disconnect with each other.

FIGS. 5E to 5H show that one of the four blocks of the code-recognition element (30) independently disconnects with others while other blocks connect with each other.

FIG. 5E shows a form of code-recognition element (30E) corresponding to a fifth set of calibration code, and the first block (31) of the code-recognition element (30E) disconnects with others independently while the second block (32), the third block (33) and the fourth block (34) of the code-recognition element (30E) connect with each other.

FIG. 5F shows a form of code-recognition element (30F) corresponding to a sixth set of calibration code, and the third block (33) of the code-recognition element (30F) disconnects with others independently while the first block (31), the second block (32) and the fourth block (34) of the code-recognition element (30F) connect with each other.

FIG. 5G shows a form of code-recognition element (30G) corresponding to a seventh set of calibration code, and the fourth block (34) of the code-recognition element (30G) disconnects with others independently while the first block (31), the second block (32) and the third block (33) of the code-recognition element (30G) connect with each other.

FIG. 5H shows a form of code-recognition element (30H) corresponding to a eighth set of calibration code, and the second block (32) of the code-recognition element (30H) disconnects with others independently while the first block (31), the third block (33) and the fourth block (34) of the code-recognition element (30H) connect with each other.

FIGS. 5I to 5N show that two of the four blocks of the code-recognition element (30) connect with each other and the other two independently disconnect with others.

FIG. 5J shows a form of code-recognition element (30I) corresponding to a ninth set of calibration code, and the first block (31) and the second block (32) of the code-recognition element (30H) connect with each other while the third block (33) and the fourth block (34) of the code-recognition element (30H) disconnect independently with others.

FIG. 5J shows a form of code-recognition element (30J) corresponding to a tenth set of calibration code, and the third block (33) and the fourth block (34) of the code-recognition element (30J) connect with each other while the first block (31) and the second block (32) of the code-recognition element (30J) disconnect independently with others.

FIG. 5K shows a form of code-recognition element (30K) corresponding to an eleventh set of calibration code, and the third block (33) and the first block (31) of the code-recognition element (30K) connect with each other while the second block (32) and the fourth block (34) of the code-recognition element (30K) disconnect independently with others.

FIG. 5L shows a form of code-recognition element (30L) corresponding to a twelfth set of calibration code, and the second block (32) and the fourth block (34) of the code-recognition element (30L) connect with each other while the first block (31) and the third block (33) of the code-recognition element (30L) disconnect independently with others.

FIG. 5M shows a form of code-recognition element (30M) corresponding to a thirteenth set of calibration code, and the second block (32) and the third block (33) of the code-recognition element (30M) connect with each other while the first block (31) and the fourth block (34) of the code-recognition element (30M) disconnect independently with others.

FIG. 5N shows a form of code-recognition element (30N) corresponding to a fourteenth set of calibration code, and the first block (31) and the fourth block (34) of the code-recognition element (30N) connect with each other while the second block (32) and the third block (33) of the code-recognition element (30N) disconnect independently with others.

The code-recognition element (30) of the electrochemical biosensor strip in accordance with the present invention is composed of conducting materials. In a preferred embodiment, the code-recognition element (30) is composed of carbon.

When the electrochemical biosensor strip with a specific form of code-recognition element (30) couples to a biosensing device, the device will automatically choose a specific set of calibration code corresponding to the specific form of the code-recognition element (30) by identifying the connection or disconnection among blocks.

Figure 6A:
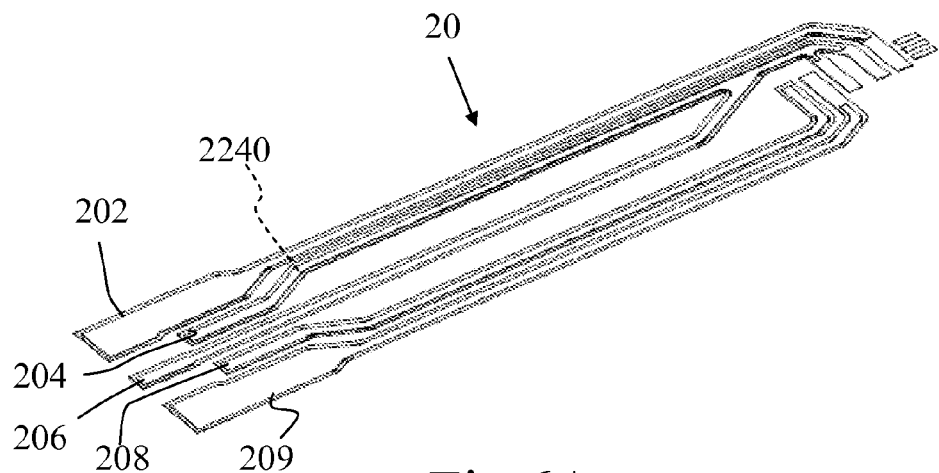
FIG. 6A is a view of a first form of an electrode system of an electrochemical biosensor strip in accordance with the present invention.

With reference to FIG. 6A, FIG. 6A is a view of a first form of the electrode system of an electrochemical biosensor strip in accordance with the present invention. FIGS. 6B to 6E are forms of the length-changeable area (2240) of the second electrode of silver layer (22) referring to FIG. 6A, and the silver layer (22) is shown by dotted line and the carbon layer (24) is shown by solid line.

In a preferred embodiment, the second electrode of the electrode system (204) and the third electrode of the electrode system (206) connect with each other and regarded as a reference electrode, and the second electrode of silver layer (224) has a length-changeable area (2240). Because of the difference of the length of each electrode, the resistance value of each electrode can be different. Therefore, a corresponding biosensing device can be identified due to different resistance values of each electrode.

In a more preferred embodiment, four forms of length-changeable area (2240) of the second electrode of the silver layer can be formed.

Figures 6B, 6C, 6D, 6E:
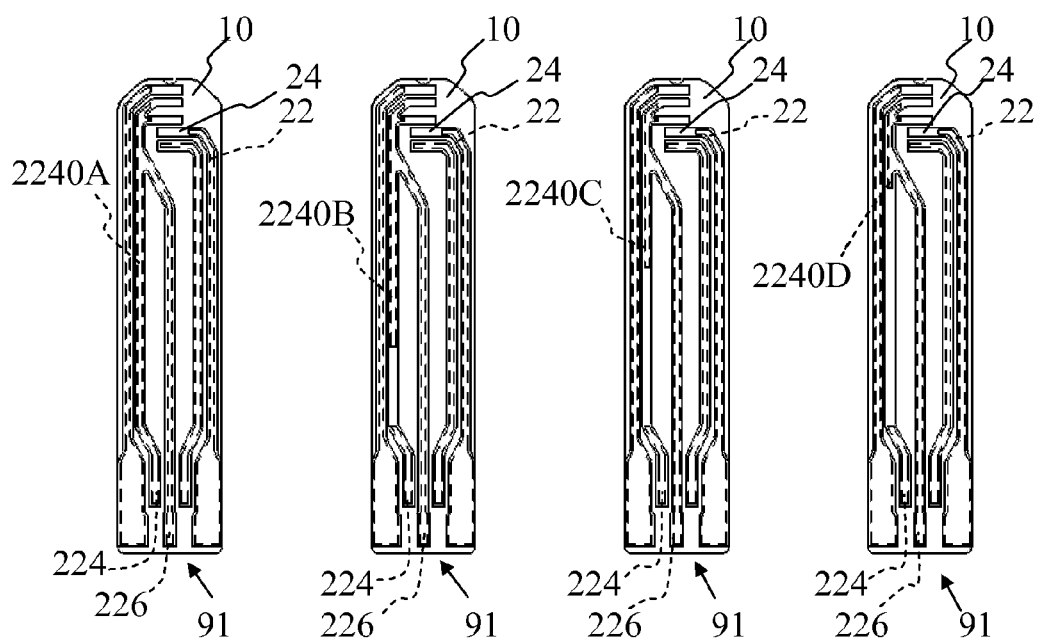
FIGS. 6B to 6E are exploded views of forms of a length-changeable area of a second electrode of a silver layer referring to FIG. 6A.

FIG. 6B shows that a length-changeable area of the second electrode of the silver layer (2240A) is full-length long and connects to the second electrode of the silver layer (224) at the sensor end (91)

FIG. 6C shows that a length-changeable area of the second electrode of the silver layer (2240B) is two-thirds of full length long and disconnects to the second electrode of the silver layer (224) at the sensor end (91).

FIG. 6D shows that a length-changeable area of the second electrode of the silver layer (2240C) is one-third of full length long and disconnects to the second electrode of the silver layer (224) at the sensor end (91).

FIG. 6E shows that a length-changeable area of the second electrode of the silver layer (2240E) is completely emptied out and disconnects to the second electrode of the silver layer (224) at the sensor end (91).

According to the specification described above, the resistance value of the second electrode of the electrode system (204) is directly proportional to the emptied-length of the length-changeable area of the electrode of the silver layer (2240).

When the strip couples to a biosensing device, the device may recognize the difference of the resistance value due to different length of the length-changeable area of the second electrode of the silver layer (2240), and it can confirm whether the strip is the specific one corresponding to the device or not.

Figure 7A:
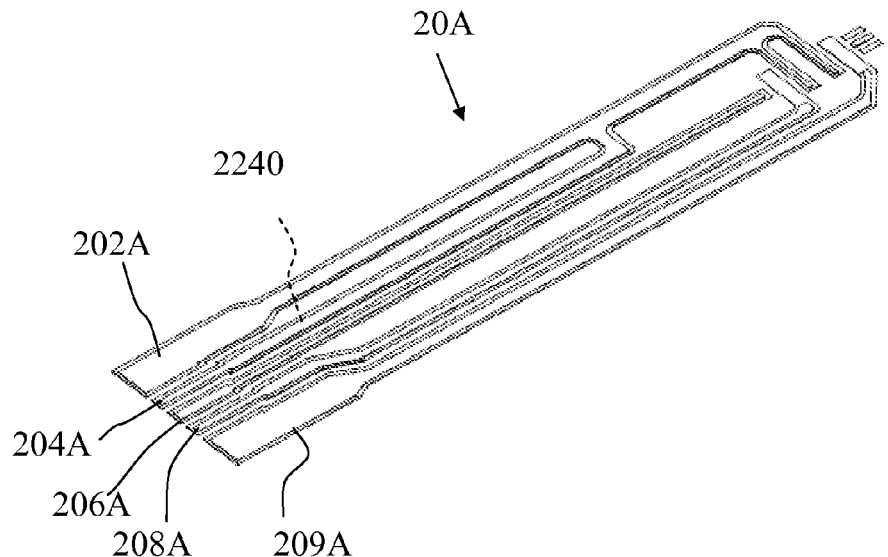
FIG. 7A is a view of a second form of an electrode system of an electrochemical biosensor strip in accordance with the present invention.

FIG. 7A is a view of a second form of the electrode system of an electrochemical biosensor strip in accordance with the present invention. Referring to FIG. 7A, the first electrode of the electrode system (202A) and the second electrode of the electrode system (204A) connect with each other to form a short circuit and regarded as a reference electrode, the third electrode of the electrode system (206A) is regarded as a detecting electrode, the fourth electrode of the electrode system (208A) is regarded as a working electrode for measuring the concentration of the blood glucose, and the fifth electrode of the electrode system (209A) is regarded as a working electrode for measuring the blood hematocrit in a sample.

Referring to FIGS. 7B to 7E, they are forms of the length-changeable area of the second electrode of silver layer according to the FIG. 7A, and the second electrode of the silver layer (224A) has a length-changeable area (2240).

Preferably, four forms of the length-changeable area of the second electrode of the silver layer (2240) can be formed.

Figures 7B, 7C, 7D, 7E:
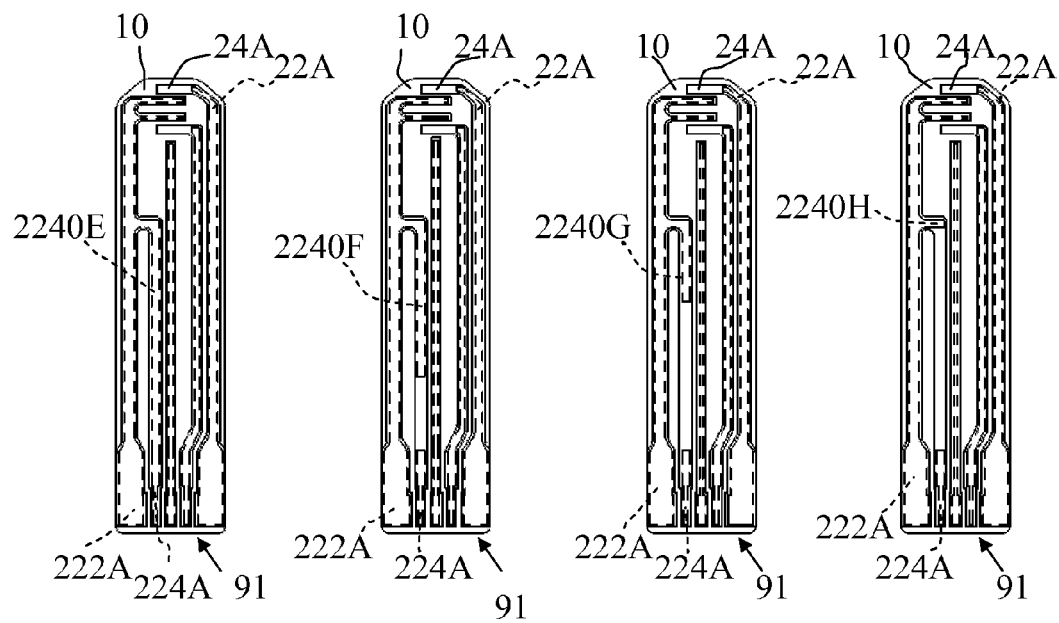
FIGS. 7B to 7E are exploded views of forms of a length-changeable area of a second electrode of the silver layer referring to FIG. 7A.

FIG. 7B shows that a length-changeable area of the second electrode of the silver layer (2240E) which is full-length long and connects to the second electrode of the silver layer (224A) at the sensor end (91).

FIG. 7C shows that a length-changeable area of the second electrode of the silver layer (2240F) is two-thirds of full length long and disconnects to the second electrode of the silver layer (224A) at the sensor end (91).

FIG. 7D shows that a length-changeable area of the second electrode of the silver layer (2240G) is one-third of full length long and disconnects to the second electrode of the silver layer (224A) at the sensor end (91).

FIG. 7E shows that a length-changeable area of the second electrode of the silver layer (2240H) is completely emptied out and disconnects to the second electrode of the silver layer (224A) at the sensor end (91).

Figure 8:
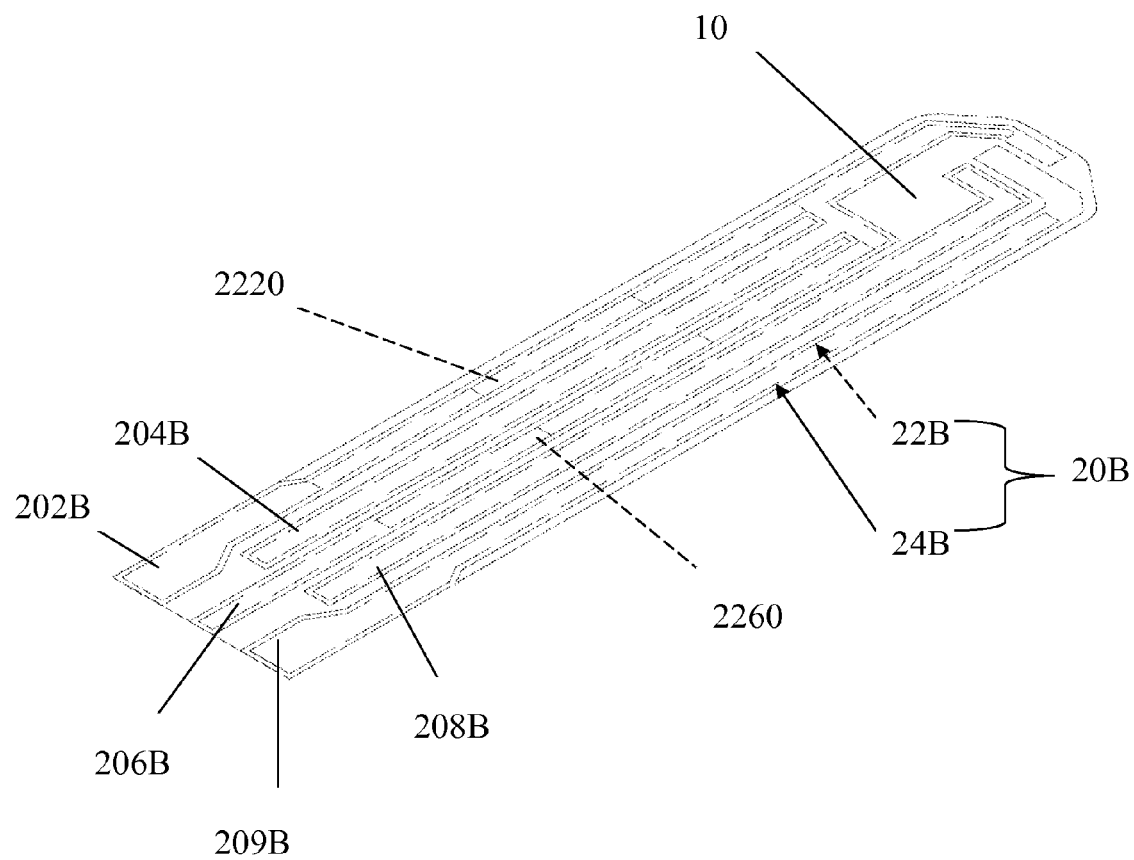
FIG. 8 is a view of a third electrode system of an electrochemical biosensor strip in accordance with the present invention

FIG. 8 is a view of a third form of the electrode system of an electrochemical biosensor strip in accordance with the present invention. Referring to FIG. 8, in a preferred embodiment, the electrode system (20B) comprises three electrodes, and at least two of them have a length-changeable area (2220, 2260) respectively. As described herein, the electrode system (20B) includes a silver layer (22B) and a carbon layer (24B) that are disposed in parallel connection to form each electrode of the electrode system (20B). Herein, the dotted line represents the silver layer (22B) and the solid line represents the carbon layer (24B).

In another preferred embodiment referring to FIG. 8, the electrode system includes five electrodes from one side to another side in a order named first electrode of the electrode system (202B), second electrode of the electrode system (204B), third electrode of the electrode system (206B), fourth electrode of the electrode system (208B) and fifth electrode of the electrode system (209B), and the first electrode, the second electrode and the third electrode of the electrode system (202B, 204B, 206B) connect with each other to form a short circuit. Two of the five electrodes have a length-changeable area (2220, 2260) respectively and the length-changeable area (2220, 2260) is part of the silver layer (22B).

Figure 9:
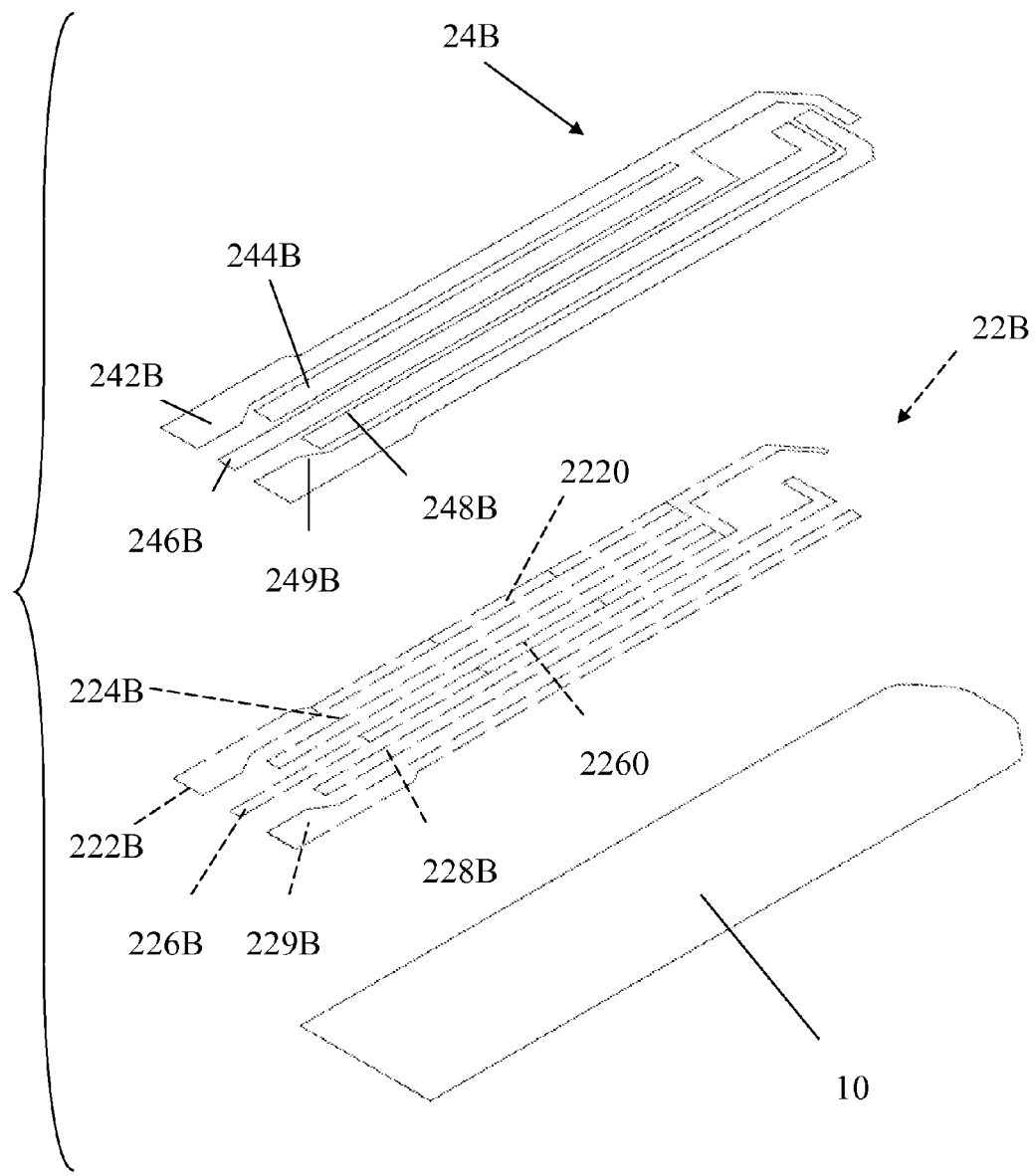
FIG. 9 is a perspective view of the third electrode system of an electrochemical biosensor strip referring to FIG. 8.

FIG. 9 is a perspective view of the third form of the electrode system of an electrochemical biosensor strip according to FIG. 8.

In another preferred embodiment referring to FIG. 9, each electrode of the electrode system includes a correlated electrode of the carbon layer and a correlated electrode of the silver layer. The five correlated electrodes of the silver layer respectively named first electrode of the silver layer (222B), second electrode of the silver layer (224B), third electrode of the silver layer (226B), fourth electrode of the silver layer (228B) and fifth electrode of the silver layer (229B). The five correlated electrodes of the carbon layer respectively named first electrode of the carbon layer (242B), second electrode of the carbon layer (244B), third electrode of the carbon layer (246B), fourth electrode of the carbon layer (248B) and fifth electrode of the carbon layer (249B).

Referring to FIGS. 8 and 9, the first electrode of the electrode system (202B) includes the first electrode of the silver layer (222B) and the first electrode of the carbon layer (242B); the second electrode of the electrode system (204B)

includes the second electrode of the silver layer (224B) and the second electrode of the carbon layer (244B), and so does others.

In another preferred embodiment of the present invention, the first electrode of the silver layer (222B) has a length-changeable area (2220) and the third electrode of the silver layer (226B) has a length-changeable area (2260). More preferably, four forms of the length-changeable area (2220) of the first electrode of the silver layer (222B) and four forms of the length-changeable area (2260) of the third electrode of the silver layer (226B) can be formed respectively.

FIGS. 10A to 10P are some forms of the electrodes of the third form of the electrode system referring to FIG. 8.

As FIGS. 10A to 10P showed, four forms of the length-changeable area (2220) of the first electrode of the silver layer (222B) and four forms of the length-changeable area (2260) of the third electrode of the silver layer (226B) can be formed respectively which are full length long (2220A, 2260A), two-thirds of the full length long (2220B, 2260B), one-third of the full length long (2220C, 2260C) and emptied of the full length long (2220D, 2260D). Hence, sixteen forms of electrode systems can be formed respectively and each of them can correspond to a particular biosensing device.

Take FIG. 10B for instance, the length-changeable area of the first electrode of the silver layer (2220A) is full length long and the length-changeable area of the third electrode of the silver layer (2260B) is two-thirds of the full length long; another instance referring to FIG. 10C show that the length-changeable area of the first electrode of the silver layer (2220A) is full length long and the length-changeable area of the third electrode of the silver layer (2260C) is one-third of the full length long.

As described in specification and in forward embodiments, there is a ratio of the length of the length-changeable area (2220) of the first electrode of the silver layer (222B) and that of the length-changeable area (2260) of the third electrode of the silver layer (226B). As described in the specification, the embodiments showed a ratio of the lengths of the length-changeable area of the two electrodes. Take FIG. 10B for instance, the ratio is 3:2; as in FIG. 10C, the ratio is 3:1. In above embodiments, the ratio can be one of the ratios in a range of 1:10 to 10:1. In another preferred embodiment, the ratio can be one of the ratios in a range of 1:4 to 4:1. The ratio is used for identifying a biosensing device corresponding to the strip.

Figure 11:
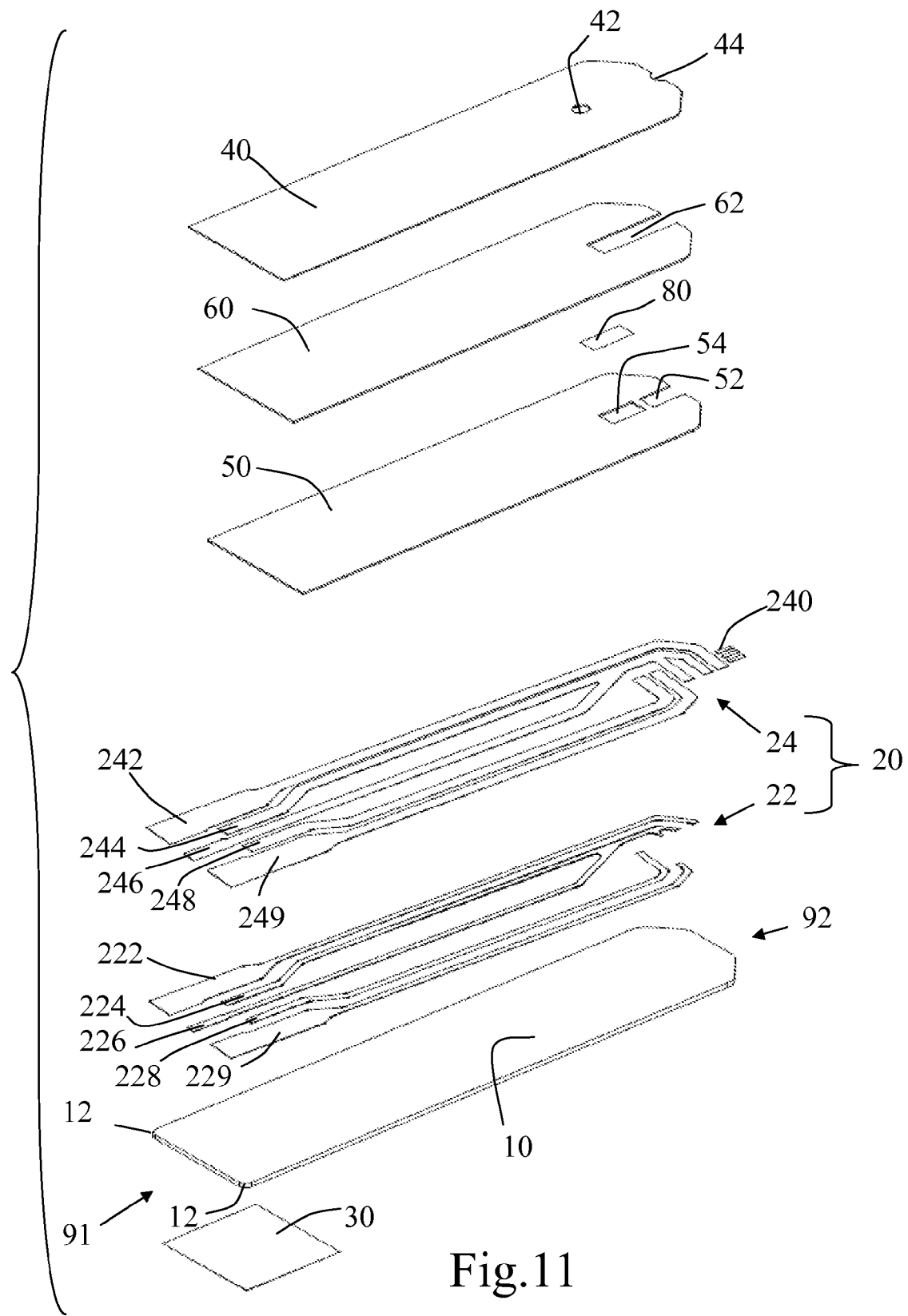
FIG. 11 is an exploded perspective view of a more preferred embodiment of the present invention.

Referring to FIG. 11, it is an exploded perspective view of a more preferred embodiment of the present invention. As FIG. 11 shows, the electrochemical biosensor strip in accordance with the present invention further comprises an isolation layer (50) laid onto the electrode system (20) and part of the base (10). The isolation layer (50) at the reaction end (92) has a first recess (52) opening toward the reaction end (92) in a longitudinal direction. The isolation layer (50) further has an opening (54) next to the first recess (52) which corresponds to the reaction area (80) and disconnects with the first recess (52).

In a more preferred embodiment referring to FIG. 11, the carbon layer (24) has a rough unit (240) at an outer side at the reaction end (92), and preferably formed as one straight line or multiple straight lines. The rough unit (240) is made of conducing materials, preferably is made of carbon. The rough unit (240) can be also made of non-conducting materials. The rough unit (240) is used for increasing the roughness of the base (10), preventing the material at the reaction area (80) from separating apart and for increasing the accuracy of measurement. More preferably, the rough unit (240) is located near the outer side of the reaction area (80).

The electrochemical biosensor strips in accordance with the present invention further comprises a glue layer (60) laid between the isolation layer (50) and the cover (40) for joining the isolation layer (50) and the cover (40) together. The glue layer (60) has a second recess (62) corresponding to the first recess (52) and to the opening (54) at the isolation layer (50). Preferably, the glue layer (60) is composed of polyethylene terephthalate or PET and coated with sticky materials such as hydrogel over its top side and bottom side for sticking the isolation layer (50) and the cover (40) together.

Figure 12:
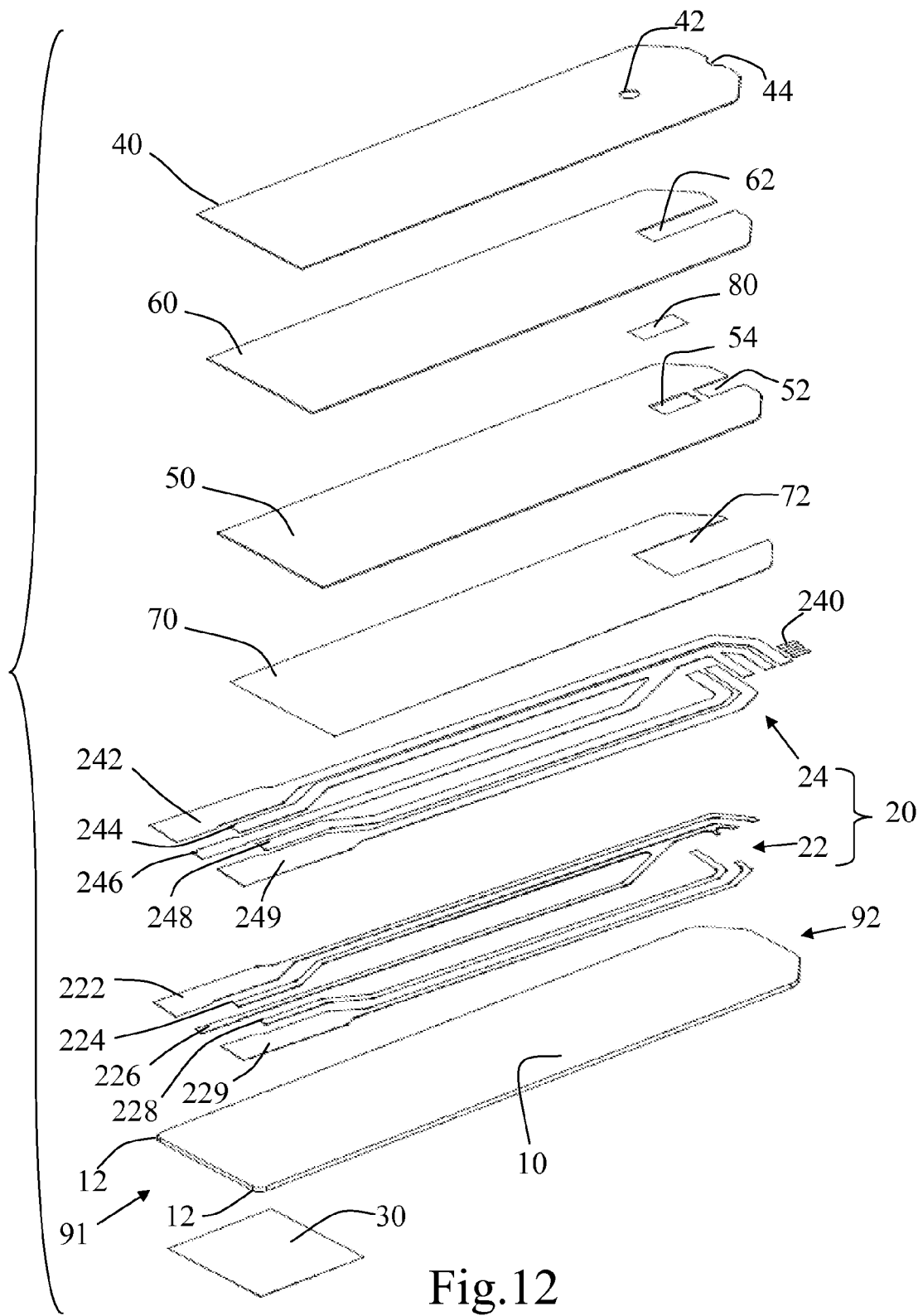
FIG. 12 is an exploded perspective view of another more preferred embodiment of present invention.

FIG. 12 is an exploded perspective view of another more preferred embodiment of the present invention.

Referring to FIG. 12, the electrochemical biosensor strip in accordance with the present invention further comprises an insulating layer (70) laid between the electrode system (20) and the isolation layer (50). The insulating layer (70) has a third recess (72) corresponding to the first recess (52) and to the opening (54) at the isolation layer (50).

Besides, a method in accordance with the present invention is provided for identifying a corresponding biosensing device by using the strip with at least two electrodes of the electrode system (20B) having a length-changeable area respectively.

Figure 13:
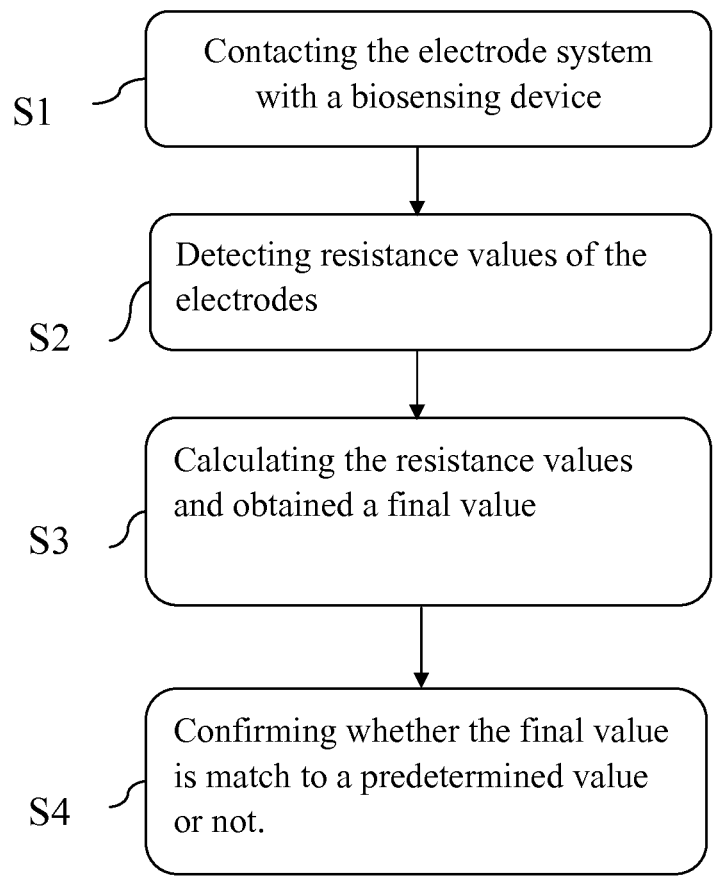
FIG. 13 is a flow chart illustrating steps of a preferred embodiment of a method in accordance with the present invention.

FIG. 13 is a flow chart illustrating steps of a preferred embodiment of the method of the present invention. Referring to FIG. 13, a preferred embodiment of the method includes step 1 (S1): contacting the electrode system (20B) with a biosensing device, step 2 (S2): detecting resistance values of the electrodes having the length-changeable area respectively and obtained the resistance values, step 3 (S3): calculating the resistance values according to a formula and obtained a final value, and step 4(S4): confirming whether the final value is match to a predetermined value of the biosensing device or not.

The term "contact with" herein in step 1(S1) means, but is not limited, to connect the electrode system (20B) and the biosensing device, or to electrically connect the electrode system (20B) and the biosensing device. The formula described in step 3 (S3) can be any mathematical operation that people skilled in the art such as, but not limited, four arithmetic operations or the combination thereof. The predetermined value described in step 4(S4) is set previously in the memory of the biosensing device. The predetermined value can be set differently depending on the need, purpose, analyte, customer or users. The final value is used for identifying a biosensing device corresponding to the strip.

Figure 14:
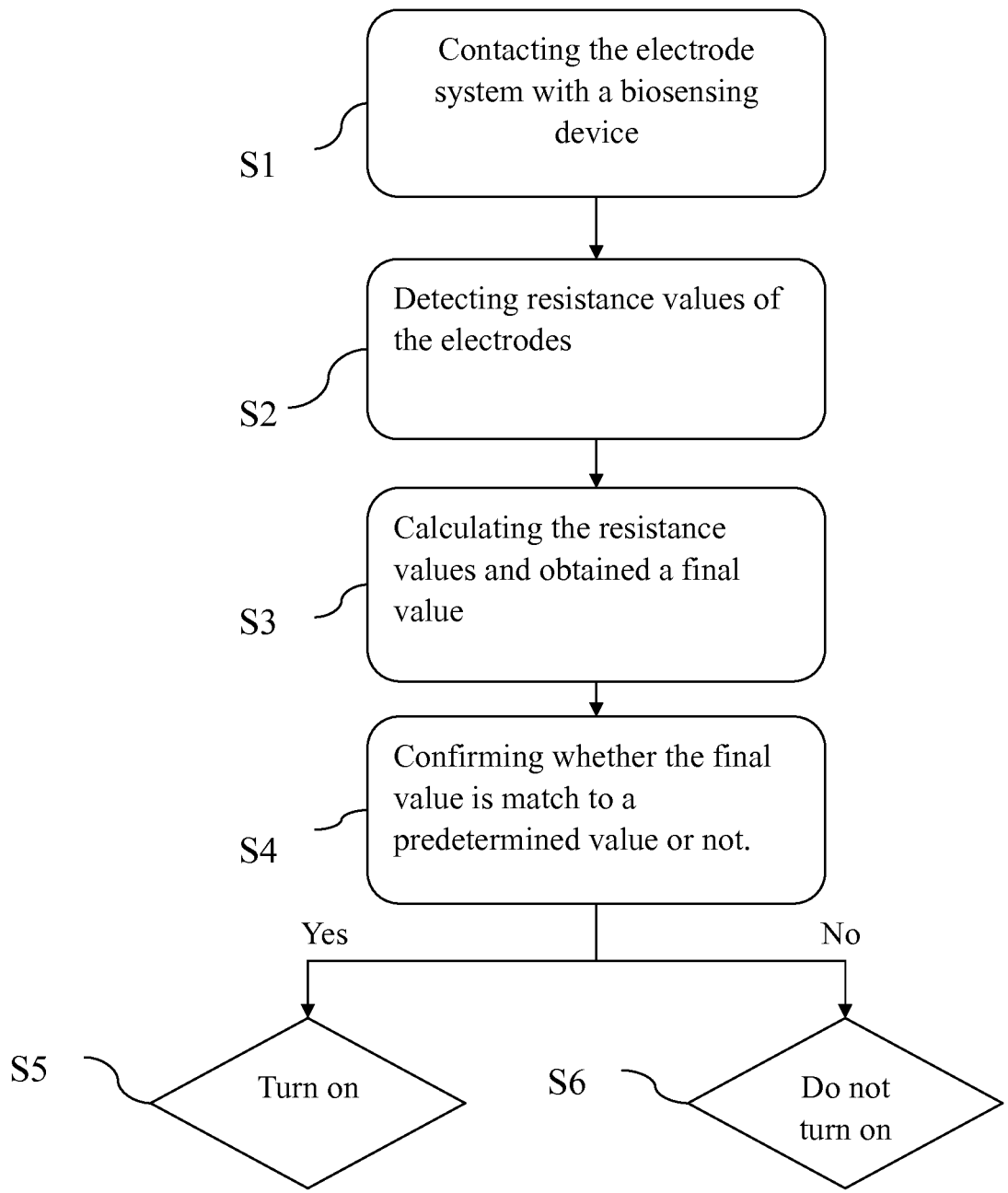
FIG. 14 is a flow chart illustrating steps of another preferred embodiment of a method in accordance with the present invention.

FIG. 14 is a flow chart illustrating steps of another preferred embodiment of the method of the present invention. Referring to FIG. 14, the method further includes steps which are turning on the biosensing device (S5) if the final value is match to the predetermined value, and do not turning on the biosensing device (S6) if the final value is not match to the predetermined value.

Figure 15:
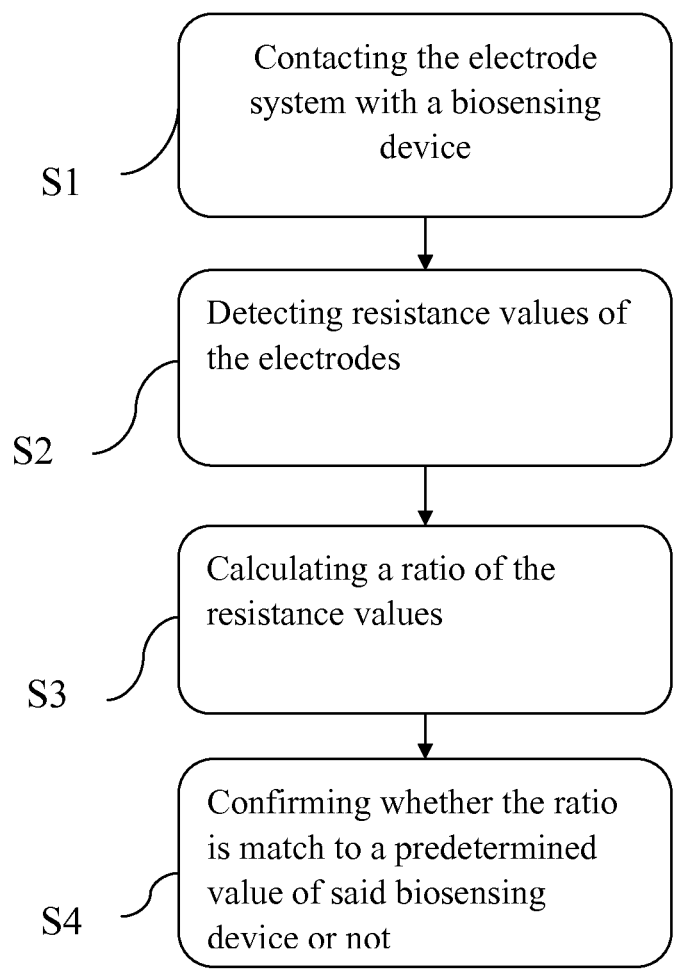
FIG. 15 is a flow chart illustrating steps of a more preferred embodiment of a method in accordance with the present invention.

FIG. 15 is a flow chart illustrating steps of a more preferred embodiment of the method of the present invention. Referring to FIG. 15, the provided method for identifying a biosensing device by using the strip with at least two electrodes of the electrode (20B) respectively having a length-changeable area includes step 1 (S1A): contacting the electrode system (20B) with a biosensing device, step 2 (S2A): detecting resistance values of the two electrode having the length-changeable area respectively and obtained a first resistance value and a second resistance value, step 3 (S3A): calculating a ratio of the first resistance value and the second resistance value, and step 4 (S4A): confirming whether the ratio is match to a predetermined value of the biosensing device or not.

The term "contact with" herein in step 1 (S1A) means, but is not limited, to connect the electrode system (20B) and the biosensing device, or to electrically connect the electrode system (20B) and the biosensing device.

The first resistance value and the second resistance value respectively do not correlate to a particular electrode having a length-changeable area. Take FIG. 8 for instance, if the resistance value of the first electrode of the electrode system (202B) is regarded as the first resistance value, then the resistance value of the third electrode of the electrode system (206B) is regarded as the second resistance value; If the resistance value of the third electrode of the electrode system (206B) is regarded as the first resistance value, then the resistance value of the first electrode of the electrode system (202B) is regarded as the second resistance value.

The ratio described in step 3 (S3A) can be the first resistance value divided by the second resistance value (the first resistance value/the second resistance value) or can be the second resistance value divided by the first resistance value (the second resistance value/the first resistance value).

The predetermined value described in step 4 (S4A) is set previously in the memory of the biosensing device. The predetermined value can be set differently depending on the need, purpose, analyte, customer or users. The ratio is used for identifying a biosensing device corresponding to the strip.

According to the specification described above, the first resistance value and the second resistance value are in direct proportion to the emptied-lengths of the length-changeable area of the two electrodes respectively. Therefore, the ratio of the two resistance value is near equal to the ratio of the emptied-lengths of the length-changeable area of the two electrodes. Take FIG. 10F as an example, the ratio is 1; Take FIG. 10G as an example, the ratio can be 0.5 or 2. The rest may be deduced by analogy.

Figure 16:
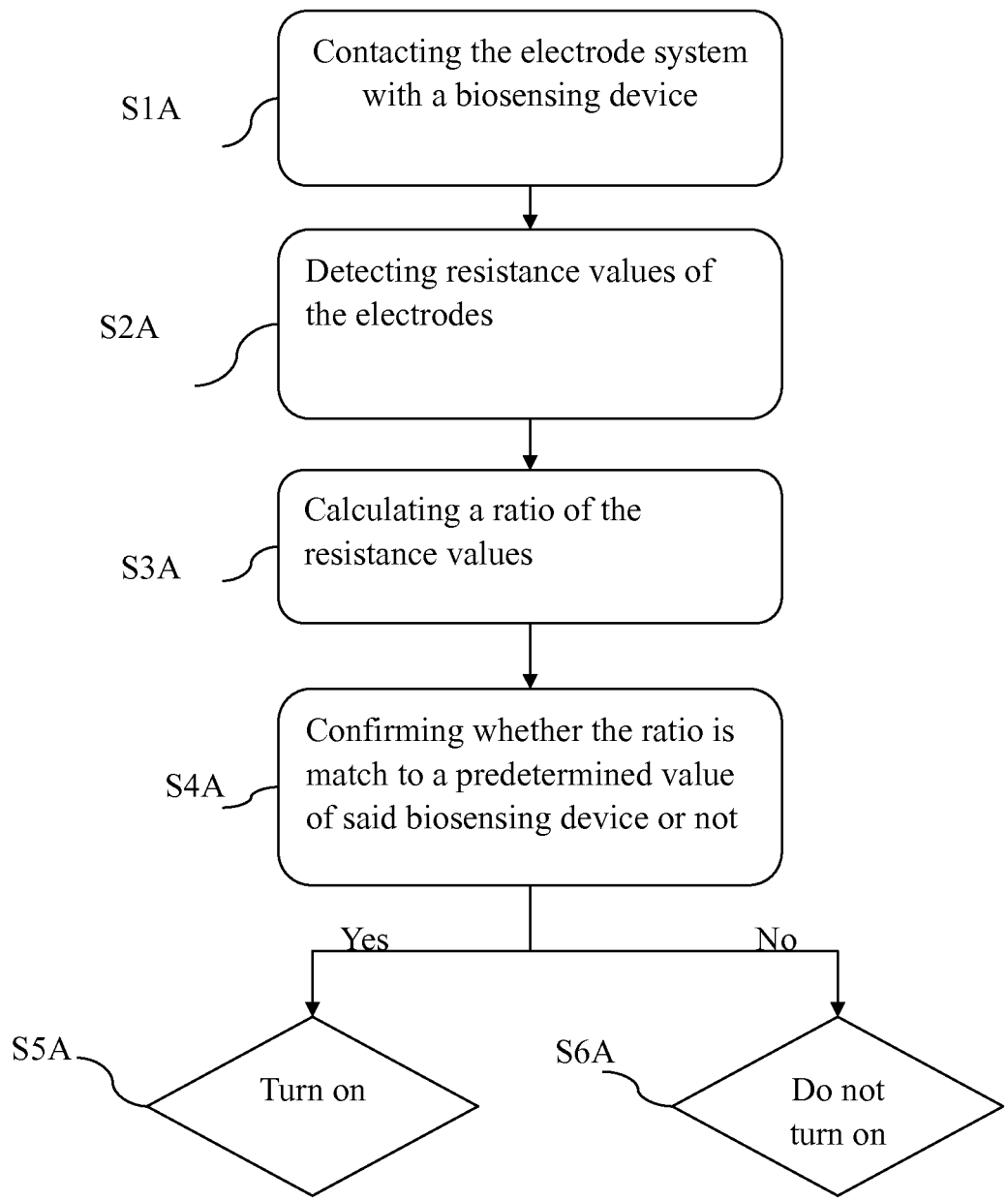
FIG. 16 is a flow diagram illustrating steps of another more preferred embodiment of the method of the present invention.

FIG. 16 is a flow chart illustrating steps of another more preferred embodiment of the method of the present invention. Referring to FIG. 15 and FIG. 16, the method further includes steps which are turning on the biosensing device (S5A) if the ratio is match to the predetermined value, and do not turning on the biosensing device (S6A) if the ratio is not match to the predetermined value.

Other embodiments of the invention will appear to those skilled in the art from consideration of the specification and practice of the invention disclosed herein. It is intended that the specification and examples to be considered as exemplary only, with a true scope and spirit of the invention being indicated by the following claims.

What is claimed is:

1. An electrochemical biosensor strip comprising:
   a base;
   an electrode system laid on the base and comprising at least two electrodes and at least one of the electrodes has a length-changeable area used for identifying a biosensing device corresponding to the electrochemical biosensor strip;
   a cover located on the electrode system; and
   a reaction area touched with the electrode system for a reaction to take place,
   wherein the electrode having the length-changeable area is a reference electrode, said reference electrode is configured to be short circuited for identifying said biosensing device corresponding to the strip.

2. The electrochemical biosensor strip of claim 1, wherein there is four forms of lengths of the length-changeable area.

3. The electrochemical biosensor strip of claim 1, wherein at least two electrodes of the electrode system have a length-changeable area respectively.

4. The electrochemical biosensor strip of claim 3, where there is a ratio of the lengths of the length-changeable areas.

5. The electrochemical biosensor strip of claim 4, wherein the ratio is used for identifying a biosensing device corresponding to the strip.

6. The electrochemical biosensor strip of claim 3, wherein the ratio is one of the ratios in a range of 1:10 to 10:1.

7. The electrochemical biosensor strip of claim 6, wherein the ratio is one of the ratios in a range of 1:4 to 4:1.

8. The electrochemical biosensor strip of claim 1, wherein the electrode system comprises a silver layer and a carbon layer, the carbon layer is stacked onto the silver layer, and each electrode of the electrode system includes a correlated electrode of the carbon layer and a correlated electrode of the silver layer.

9. The electrochemical biosensor strip of claim 8, wherein the electrode system includes five electrodes and two of them have a length-changeable area respectively.

10. The electrochemical biosensor strip of claim 9, wherein the length-changeable area is part of the silver layer.

11. The electrochemical biosensor strip of claim 10, where there is a ratio of the lengths of the two length-changeable areas.

12. The electrochemical biosensor strip of claim 11, wherein the ratio is used for identifying a biosensing device corresponding to the strip.

13. The electrochemical biosensor strip of claim 12, wherein the ratio is one of the ratios in a range of 1:10 to 10:1.

14. The electrochemical biosensor strip of claim 13, wherein the ratio is one of the ratios in a range of 1:4 to 4:1.

15. The electrochemical biosensor strip of claim 8, wherein the electrode system comprises five electrodes, and the five electrodes from one side to another side in an order are a first electrode, a second electrode, a third electrode, a fourth electrode and a fifth electrode, and the first electrode and the third electrode have a length-changeable area respectively.

16. The electrochemical biosensor strip of claim 15, wherein at least two electrodes of the electrode system connect with each other to form the short circuit and is regarded as said reference electrode.

17. The electrochemical biosensor strip of claim 16, wherein the first electrode, second electrode and third electrode of the electrode system connect with each other to form the short circuit and is regarded as said reference electrode.

18. The electrochemical biosensor strip of claim 1, further comprising a sensor end and a reaction end, wherein a distance between an end of the electrode system and the base at the sensor end is 0.1 to 1 millimeter.

19. The electrochemical biosensor strip of claim 1, wherein the base has a front side and a back side and the electrode system is laid on the front side of the base, and a code-recognition element laid on one end of the back side of the base for corresponding to a specific set of calibration code.

20. The electrochemical biosensor strip of claim 19, wherein the code-recognition element comprises at least two blocks and the at least two blocks connect or disconnect with each other for being recognized as one code.

21. The electrochemical biosensor strip of claim 20, wherein the code-recognition element is defined by laser etching or knife etching for shaping forms of the code-recognition element.

22. The electrochemical biosensor strip of claim 20, wherein the code-recognition element comprises at least four blocks.

23. The electrochemical biosensor strip of claim 22, wherein the code-recognition element comprises four blocks that are a first block, a second block, a third block and a fourth block respectively.

24. The electrochemical biosensor strip of claim 23, wherein the four blocks connect with each other.

25. The electrochemical biosensor strip of claim 23, wherein two of the four blocks connect with each other and the other two of the four blocks connect with each other and the two connected blocks disconnect with the other two connected blocks.

26. The electrochemical biosensor strip of claim 23, wherein the four blocks disconnect with each other.

27. The electrochemical biosensor strip of claim 23, wherein one of the four blocks disconnects independently with any other blocks and the other three of the four blocks connect with each other.

28. The electrochemical biosensor strip of claim 23, wherein two of the four blocks connect with each other and the other two of the four blocks disconnect independently with any other blocks.

29. The electrochemical biosensor strip of claim 23, wherein the code-recognition element is composed of conducting materials.

\* \* \* \* \*